(12) United States Patent
Mates et al.

(10) Patent No.: US 10,597,394 B2
(45) Date of Patent: Mar. 24, 2020

(54) ORGANIC COMPOUNDS

(71) Applicant: INTRA-CELLULAR THERAPIES, INC., New York, NY (US)

(72) Inventors: Sharon Mates, New York, NY (US); Peng Li, New Milford, NJ (US); Lawrence P. Wennogle, Hillsborough, NJ (US); Robert Davis, San Diego, CA (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 16/054,728

(22) Filed: Aug. 3, 2018

(65) Prior Publication Data

US 2019/0062334 A1 Feb. 28, 2019

Related U.S. Application Data

(63) Continuation of application No. 15/301,912, filed as application No. PCT/US2015/024340 on Apr. 3, 2015, now Pat. No. 10,077,267.

(60) Provisional application No. 61/975,610, filed on Apr. 4, 2014.

(51) Int. Cl.

| | | |
|---|---|---|
| *C07D 471/16* | (2006.01) |
| *A61K 31/4985* | (2006.01) |
| *A61P 25/18* | (2006.01) |
| *A61P 25/22* | (2006.01) |
| *A61P 25/24* | (2006.01) |
| *C07D 471/14* | (2006.01) |
| *A61K 45/06* | (2006.01) |
| *C07B 59/00* | (2006.01) |

(52) U.S. Cl.
CPC ........ *C07D 471/16* (2013.01); *A61K 31/4985* (2013.01); *A61K 45/06* (2013.01); *A61P 25/18* (2018.01); *A61P 25/22* (2018.01); *A61P 25/24* (2018.01); *C07B 59/002* (2013.01); *C07D 471/14* (2013.01)

(58) Field of Classification Search
CPC .............. C07D 471/16; A61K 31/4995; A61K 31/4985; A61P 25/18; A61P 25/22; A61P 25/24
USPC ......................................... 544/343; 514/250
See application file for complete search history.

(56) References Cited

U.S. PATENT DOCUMENTS

| | | |
|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,136,145 A | 1/1979 | Fuchs et al. |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,849,246 A | 7/1989 | Schmidt |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,538,739 A | 7/1996 | Bodmer et al. |
| 5,576,460 A | 11/1996 | Buchwald et al. |
| 5,629,003 A | 5/1997 | Horstmann et al. |
| 5,648,539 A | 7/1997 | Goodbrand |
| 5,648,542 A | 7/1997 | Goodbrand et al. |
| 5,654,482 A | 8/1997 | Goodbrand |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,763,476 A | 6/1998 | Delbressine et al. |
| 5,847,166 A | 12/1998 | Buchwald et al. |
| 5,902,901 A | 5/1999 | Goodbrand et al. |
| 5,948,430 A | 9/1999 | Zerbe et al. |
| 6,043,370 A | 3/2000 | Kubo et al. |
| 6,166,226 A | 12/2000 | Buchwald et al. |
| 6,221,335 B1 | 4/2001 | Foster |
| 6,235,936 B1 | 5/2001 | Buchwald et al. |
| 6,307,087 B1 | 10/2001 | Buchwald et al. |

(Continued)

FOREIGN PATENT DOCUMENTS

| | | |
|---|---|---|
| CN | 102105059 A | 6/2011 |
| CN | 103209704 A | 7/2013 |

(Continued)

OTHER PUBLICATIONS

Howland, R.H., "Deuterated Drugs," *Journal of Psychosocial Nursing and Mental Health Services*, 53(9): 13-16 (2015).
Kahn, A., et al., "Residual Symptoms of Schiziphrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Schennach, et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.
Timmins, G.S., "Deuterated drugs: where are we now?" *Expert Opinion on Therapeutic Patents*, 1-9 (2014).
Alvir, et al., "Clozapine-Induced Agranulocytosis," *The New England Journal of Medicine*, vol. 329, No. 3, pp. 162-167, (1993).

(Continued)

*Primary Examiner* — Venkataraman Balasubramanian
(74) *Attorney, Agent, or Firm* — Hoxie & Associates LLC

(57) ABSTRACT

This invention relates to particular substituted heterocycle fused gamma-carbolines, their prodrugs, in free, solid, pharmaceutically acceptable salt and/or substantially pure form as described herein, pharmaceutical compositions thereof, and methods of use in the treatment of diseases involving 5-HT$_{2A}$ receptor, serotonin transporter (SERT) and/or pathways involving dopamine D$_1$/D$_2$ receptor signaling systems, and/or the treatment of residual symptoms.

13 Claims, No Drawings

(56) References Cited

U.S. PATENT DOCUMENTS

| | | | |
|---|---|---|---|
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,440,710 B1 | 8/2002 | Keinan et al. |
| 6,465,693 B2 | 10/2002 | Buchwald et al. |
| 6,541,639 B2 | 4/2003 | Zhou et al. |
| 6,544,559 B2 | 4/2003 | Mesens et al. |
| 6,548,493 B1 | 4/2003 | Robichaud et al. |
| 6,552,017 B1 | 4/2003 | Robichaud et al. |
| 6,552,024 B1 | 4/2003 | Chen et al. |
| 6,603,008 B1 | 8/2003 | Ando et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,517,990 B2 | 4/2009 | Ito et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,309,772 B2 | 11/2012 | Weiner et al. |
| 8,414,922 B2 | 4/2013 | Bryson et al. |
| 8,461,148 B2 | 6/2013 | Hollander |
| 8,598,119 B2 | 12/2013 | Mates et al. |
| 8,603,514 B2 | 12/2013 | Yang et al. |
| 8,648,077 B2 | 2/2014 | Tomesch et al. |
| 8,652,378 B1 | 2/2014 | Yang et al. |
| 8,697,700 B2 | 4/2014 | Surman et al. |
| 8,779,139 B2 | 7/2014 | Tomesch et al. |
| 8,791,138 B2 | 7/2014 | Seeman et al. |
| 8,835,459 B2 | 9/2014 | Kottayil et al. |
| 8,900,497 B2 | 12/2014 | Yang et al. |
| 8,900,498 B2 | 12/2014 | Yang et al. |
| 8,906,277 B2 | 12/2014 | Yang et al. |
| 8,993,572 B2 | 3/2015 | Mates et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,216,175 B2 | 12/2015 | Amancha et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,428,506 B2 | 8/2016 | Mates et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,077,267 B2* | 9/2018 | Mates .................. C07B 59/002 |
| 10,322,134 B2 | 7/2019 | Vanover et al. |
| 2001/0008942 A1 | 7/2001 | Buchwald et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2005/0166771 A1 | 8/2005 | Gygi et al. |
| 2005/0222209 A1 | 10/2005 | Zeldis et al. |
| 2006/0205787 A1 | 9/2006 | Muller et al. |
| 2007/0082929 A1 | 4/2007 | Gant et al. |
| 2007/0197695 A1 | 8/2007 | Potyen et al. |
| 2008/0069885 A1 | 3/2008 | Mesens et al. |
| 2008/0132552 A1 | 6/2008 | Kleinman et al. |
| 2008/0280941 A1 | 11/2008 | Lourtie |
| 2009/0076159 A1 | 3/2009 | Czarnik |
| 2009/0209608 A1 | 8/2009 | Czarnik |
| 2010/0159033 A1 | 6/2010 | Gant et al. |
| 2012/0196814 A1 | 8/2012 | Gong et al. |
| 2014/0080816 A1 | 3/2014 | Koolman et al. |
| 2015/0072964 A1 | 3/2015 | Mates et al. |
| 2015/0080404 A1 | 3/2015 | Mates et al. |
| 2016/0354315 A1 | 12/2016 | Li |
| 2017/0114037 A1 | 4/2017 | Davis et al. |
| 2017/0189398 A1 | 7/2017 | Mates et al. |
| 2017/0283417 A1 | 10/2017 | Li et al. |
| 2017/0319580 A1 | 11/2017 | Yao et al. |
| 2018/0044337 A1 | 2/2018 | Tomesch et al. |
| 2018/0200256 A1 | 7/2018 | Vanover et al. |
| 2019/0231780 A1 | 8/2019 | Yao et al. |

FOREIGN PATENT DOCUMENTS

| | | |
|---|---|---|
| EP | 0 058 481 | 8/1982 |
| EP | 0 856 508 | 8/1998 |
| EP | 0 976 732 | 2/2000 |
| EP | 1 245 553 | 10/2002 |
| EP | 1 254 884 | 11/2002 |
| EP | 1 539 115 | 6/2005 |
| EP | 1 564 671 | 8/2005 |
| GB | 1476087 | 6/1977 |
| GB | 2145422 | 3/1985 |
| WO | WO 1994/024125 | 10/1994 |
| WO | WO 1995/013814 | 5/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/059129 | 8/2002 |
| WO | WO 2002/085838 | 10/2002 |
| WO | WO 2003/014118 | 2/2003 |
| WO | WO 2004/010981 | 2/2004 |
| WO | WO 2004/013094 | 2/2004 |
| WO | WO 2004/039788 | 5/2004 |
| WO | WO 2004/056324 | 7/2004 |
| WO | WO 2005/030214 | 4/2005 |
| WO | WO 2006/034187 | 3/2006 |
| WO | WO 2006/081251 | 8/2006 |
| WO | WO 2007/025103 | 3/2007 |
| WO | WO 2007/084841 | 7/2007 |
| WO | WO 2008/112280 | 9/2008 |
| WO | WO 2009/017836 | 2/2009 |
| WO | WO 2009/114181 | 9/2009 |
| WO | WO 2009/145900 | 12/2009 |
| WO | WO 2011/133224 | 10/2011 |
| WO | WO 2013/155504 | 10/2013 |
| WO | WO 2013/155505 | 10/2013 |
| WO | WO 2013/155506 | 10/2013 |
| WO | WO 2014/110322 | 7/2014 |
| WO | WO 2014/145192 | 9/2014 |
| WO | WO 2015/085004 | 6/2015 |
| WO | WO 2015/154025 | 10/2015 |
| WO | WO 2015/154030 | 10/2015 |
| WO | WO 2015/191554 | 12/2015 |
| WO | WO 2017/117514 | 7/2017 |
| WO | WO 2017/165755 | 9/2017 |

(56) References Cited

FOREIGN PATENT DOCUMENTS

| WO | WO 2017/165843 | 9/2017 |
|---|---|---|
| WO | WO 2018/106916 | 6/2018 |
| WO | WO 2018/175969 | 9/2018 |

OTHER PUBLICATIONS

Avendano, et al., "The problem of the existence of C(Ar)-H . . . N Intramolecular Hydrogen Bonds in a Family of 9-Azaphenyl-9H-carbazoles," *J. Chem. Soc. Perkin. Trans.*, vol. 2, pp. 1547-1555, (1993).
Baille, T.A., "The Use of Stable Isotopes in Pharmacological Research," *Pharmacol. Reviews*, vol. 33, No. 2, pp. 81-132, (1981).
Balbach, et al., "Pharmaceutical evaluation of early development candidates 'the 100 mg-approach'", *International Journal of Pharmaceutics*, vol. 275, pp. 1-12, (2004).
Bastin, et al.,"Salt Selection and Optimisation Procedures for Pharmaceutical New Chemical Entities", *Organic Process and Research Development*, vol. 4, No. 5, pp. 427-435 (2000).
Beletskaya, et al., "Pd- and Cu-catalyzed selective arylation of benzotriazole," *Tetrahedron Letters*, vol. 39, pp. 5617-5620, (1998).
Bennett, et al., "Cecil Textbook of Medicine," 20th Edition, vol. 1, pp. 1004-1010, (1996).
Berger, et al., "Synthesis of some conformationally restricted analogs of fentanyl." *Journal of Medicinal Chemistry*, vol. 20, No. 4, pp. 600-602, (1977).
Boger, et al., "Inverse Electron Demand Diels-Alder Reactions of Heterocyclic Aza Dienes. Studies on the Total Synthesis of Lavendamycin: Investigative Studies on the Preparation of the CDE β-Carboline Ring System and AB Quinoline-5,8-quinone Ring System" *J. Org. Chem.*, vol. 50, pp. 5782-5789, (1985).
Bowman, et al., "Intramolecular Aromatic Substitution (SRN1) Reactions—Use of Entrainment for the Preparation of Benzothiazoles," Tetrahedron Letters, vol. 23, pp. 5093-5096, (1982).
Bowman, et al., "Copper (1) Catalysed Aromatic Nucleophilic Substitution: A Mechanistic and Synthetic Comparison with the $S_{RN}1$ Reaction", *Tetrahedron Letters*, vol. 25, No. 50, pp. 5821-5824, (1984).
Bowman, et al.,"Synthesis of 1H-quinazoline-4-ones Using Intramolecular Aromatic Nucelophilic Substitution," *ARKIVOC*, vol. x, pp. 434-442 (2003).
Bremner, et al., "Neuroimaging of Posttraumatic Stress Disorder", *Psychiatric Annals Journal*, vol. 28, No. 8, p. 445-450, (1998).
Browne, T.R., "Stable Isotope Techniques in Early Drug Development: An Economic Evaluation," *J. Clin. Pharmacol.*, vol. 38, pp. 213-220, (1998).
Bryan-Lluka, et al., "Potencies of Haloperidol Metabolites as Inhibitors of the Human Noradrenaline, Dopamine and Serotonin Transporters in Transfected COS-7 Cells", *Naunyn-Shemiedeberg's Arch Pharmacol*, vol. 360, pp. 109-115, (1999).
Byrn, et al., "Pharmaceutical Solids: A Strategic Approach to Regulatory Considerations," *Pharmaceutical Research*, vol. 12, No. 7, pp. 945-954, (1995).
Caira, M.R., "Crystalline Polymorphism of Organic Compounds," *Topics in Current Chemistry*, vol. 198, p. 163-203, (1998).
Cherrah, et al., "Study of Deuterium Isotope Effects on Protein Binding by Gas Chromatography/Mass Spectrometry. Caffeine and Deuterated Isotopomers," *Biomedical and Environmental Mass Spectrometry*, vol. 14, pp. 653-657, (1987).
Crawford, et al., "Copper-Catalyzed Amidations of Bromo Substituted Furans and Thiophenes," *Tetrahedron Letters*, vol. 43, pp. 7365-7368, (2002).
Darmani, et al., "Do Functional Relationships Exist Between 5-$HT_{1A}$ and 5-$HT_2$ Receptors?" *Pharmacology and Biochemistry & Behavior*, vol. 36, pp. 901-906, (1990).
Davis, et al., "Iti-007 demonstrates brain occupancy at serotonin 5-HT2A and dopamine D2 receptors and serotonin transporters using positron emission tomography in healthy volunteers," *Psychopharmacology*, vol. 232, pp. 2863-2872, (2015); DOI: 10.1007/s00213-015-3922-1.
Davis, et al., "ITI-007 in the Treatment of Schizophrenia: From Novel Pharmacology to Clinical Outcomes," *Expert Review of Neurotherapeutics*, vol. 16, No. 6, pp. 601-614, (2016).
Dyck, et al., "Effects of Deuterium Substitution on the Catabolism of β-Phenylethylamine. An In Vivo Study," *Journal of Neurochemistry*, vol. 46, Issue 2, pp. 399-404, (1986).
Evindar, et al., "Copper- and Palladium-Catalyzed Intramolecular Aryl Guanidinylation: An Efficient Method for the Synthesis of 2-Aminobenzimidazoles", *Organic Letters*, vol. 5, No. 2, pp. 133-136, (2003).
Ezquerra, et al., "Efficient Reagents for the Synthesis of 5-, 7-, and 5, 7-Substitued Indoles Starting from Aromatic Amines. Scope and Limitations", *J. Org. Chem.*, vol. 61, pp. 5804-5812, (1996).
Fawcett, J., "Posttraumatic Stress Disorder, Stress, and Happiness", *Psychiatric Annals Journal*, vol. 28, No. 8, pp. 427-428, (1998).
Fee, et al., "Copper (II)-Promoted Solvolyses of Nickel (II) Complexes III. Tetradentate Schiff Base Ligands Containing Various Diamine Segments," *Aust. J. Chem.*, vol. 26, pp. 1475-1485, (1973).
Ferreira, et al., "Novel Synthetic Routes to Thienocarbazoles Via Palladium or Copper Catalyzed Amination or Amidation of Arylhalides and Intramolecular Cyclization", *Tetrahedron*, vol. 58, pp. 7943-7949, (2002).
Finet, et al., "Recent Advances in Ullmann Reaction: Copper (II) Diacetate Catalysed N-, )- and S-arylation Involving Polycoordinate Heteroatomic Derivatives," *Current Organic Chemistry*, vol. 6, pp. 597-626, (2002).
Friedman, M.J.., "Current and Future Drug Treatment for Posttraumatic Stress Disorder Patients", *Psychiatric Annals Journal*, vol. 28, No. 8, pp. 464-468, (1998).
Goodbrand, et al., "Ligand-Accelerated Catalysis of the Ullmann Condensation: Application to Hole Conducting Triarylamines," *J. Org. Chem.*, vol. 64, pp. 670-674, (1999).
Gouyette, A., "Synthesis of Deuterium-labelled Elliptinium and its Use in Metabolic Studies," Biomedical and Environmental Mass Spectrometry, vol. 15, pp. 243-247, (1988).
Grant, D., "Theory and Origin and Polymorphism", *Polymorphism in Pharmaceutical Solids*, Chapter 1, pp. 1-10, (1999).
Guillory, J.K., "Generation of Polymorphs, Hydrates, Solvates, and Amorphous Solids", *Polymorphism in Pharmaceutical Solids*, Chapter 5, pp. 183-226, (1999).
Hackam, et al., "Translation of Research Evidence from Animals to Humans," *JAMA*, vol. 296, No. 14, pp. 1731-1732, (2006).
Hamann, et al., "Systematic Variation of Bidentate Ligands Used in Aryl Halide Amination. Unexpected Effects of Steric, Electronic, and Geometric Perturbations", *J. Am. Chem. Soc.*, vol. 120, pp. 3694-3703, (1998).
Harbert, et al., "Neuroleptic Activity in 5-Aryltetrahydro-γ-carbolines", *J. Med. Chem.*, vol. 23, pp. 635-643, (1980).
Hartwig, J., "Palladium-Catalyzed Amination of Aryl Halides: Mechanism and Rational Catalyst Design," *Synlett*, pp. 329-340, (1996).
Harvey, et al., "Serotonin and Stress: Protective or Malevolent Actions in the Biobehavioral Response to Repeated Trauma?," *Annals of the New York Academy of Sciences*, vol. 1032, pp. 267-272, (2004); DOI: 10.1196/annals.1314.035.
Haskins, N.J., "The Application of Stable Isotopes in Biomedical Research," Biological Mass Spectrometry, vol. 9, No. 7, pp. 269-277, (1982).
Hassan, et al., "Aryl-aryl Bond Formation One Century After the Discovery of the Ullmann Reaction," *Chem. Rev.*, vol. 102, pp. 1359-1469, (2002).
Haynes, et al., "Occurrence of Pharmaceutically Acceptable Anions and Cations in the Cambridge Structural Database", *Journal of Pharmaceutical Sciences*, vol. 94, No. 10, pp. 2111-2120, (2005).
Honma, et al., "The Metabolism of Roxatidine Acetate Hydrochloride: Liberation of Deuterium from the Piperidine Ring during Hydroxylation," Drug Metabolism and Disposition, vol. 15, No. 4, pp. 551, (1987).
International Preliminary Report on Patentability for International Application No. PCT/US2013/036514 dated Oct. 14, 2014.

(56) References Cited

OTHER PUBLICATIONS

International Search Report issued in International Application No. PCT/US2008/003340, dated Aug. 8, 2008, 3 pages.
International Search Report issued in International Application No. PCT/US2009/001608, dated Apr. 27, 2009, 3 pages.
International Search Report issued in International Application No. PCT/US2009/003261, dated Jul. 16, 2009.
International Search Report issued in International Application No. PCT/US2011/00719, dated Jul. 5, 2011, 3 pages.
International Search Report issued in International Application No. PCT/US2013/036515, dated Aug. 13, 2013, 3 pages.
International Search Report issued in International Application No. PCT/US2013/036514, dated Aug. 16, 2013, 3 pages.
International Search Report issued in International Application No. PCT/US2013/036512, dated Aug. 19, 2013, 4 pages.
International Search Report issued in International Application No. PCT/US15/24340, dated Jun. 25, 2015, 2 pages.
International Search Report issued in International Application No. PCT/US15/24345, dated Jun. 25, 2015, 3 pages.
Ito, et al., "Studies of Organic Catalytic Reactions. VI. The Function of Pyridine and Copper in the Rosenmund-von Braun Reaction," *Bulletin of the Chemical Society of Japan*, vol. 41, pp. 419-423, (1968).
Izrayelit, L., "Schizoaffective Disorder and PTSD Successfully Treated With Olanzapine and Supportive Psychotherapy", *Psychiatric Annals Journal*, vol. 28, No. 8, pp. 424-426, (1998).
Jain et al., "Polymorphism in Pharmacy", *Indian Drugs*, vol. 23, No. 6, pp. 315-316, (1986).
Ji, et al., "Selective Amination of Polyhalopyridines Catalyzed by a Palladium-xantphos Complex," *Organic Letters*, vol. 5, No. 24, pp. 4611-4614, (2003).
Jordan, V.C., "Tamoxifen: A Most Unlikely Pioneering Medicine," *Nature Reviews: Drug Discovery*, vol. 2, pp. 205-213, (2003).
Juorio, A.V., et al., "Effects of Acute and Chronic Phenelzine on Regional Monoamine Metabolism in Rats and its Potentiation by Deuterium Substitution," Naunyn-Schmiedeberg's Archives of Pharmacology, vol. 333, No. 3, pp. 240-245, (1986); Abstract only.
Kametani, et al., "A Novel Synthesis of Indole Derivatives," *Heterocycles*, vol. 14 No. 3, pp. 277-280, (1980).
Kang, et al., "Copper-catalyzed N-arylation of Aryl Iodides with Benzamides or Nitrogen Heterocycles in the Presence of Ethylendiamine," *Synlett*, No. 3, pp. 427-430, (2002).
Kay, et al., "The Positive and Negative Syndrome Scale (PANSS) for Schizophrenia," *Schizophrenia Bulletin*, vol. 13, No. 2, pp. 261-276, (1987).
Kessler, et al., "Lifetime Prevalence and Age-of-Onset Distributions of DSM-IV Disorders in the National Comorbidity Survey Replication," *Arch Gen Psychiatry*, vol. 62, pp. 593-602, (2005).
Khorana, et al., "Gamma-Carbolines: Binding at 5-HT5A Serotonin Receptors," *Bioorganic & Medicinal Chemistry*, vol. 11, pp. 717-722, p. 718 Table 1, (2003).
Kiyomori, et al., "An Efficient Copper-catalyzed Coupling of Aryl Halides with Imidazoles," *Tetrahedron Letters*, vol. 40, pp. 2657-2660, (1999).
Klapars, et al., "A General and Efficient Copper Catalyst for the Amidation of Aryl Halides and the N-arylation of Nitrogen Heterocycles," *J. Am. Chem. Soc.*, vol. 123, pp. 7727-7729, (2001).
Klapars, et al., "A General and Efficient Copper Catalyst for the Amidation of Aryl Halides," *J. Am. Chem. Soc.*, vol. 124, pp. 7421-7428, (2002).
Kondratov, et al., "Nucelophilic Substitution in the Aromatic Series. Lv. Reaction of o-nitrochlorobenzene with Ammonia in the Presence of Copper Compounds," *Zhurnal Organidreskoi Khimii*, vol. 51, No. 11, pp. 2387-2390, (1979).
Koppel, et al., "Optimal Treatment of Alzheimer's Disease Psychosis: Challenges and Solutions," *Neuropsychiatric Disease and Treatment*, vol. 10, pp. 2253-2262, (2014).
Kwong, et al., "Mild and Efficient Copper-catalyzed Amination of Aryl Bromides with Primary Alkylamines," *Organic Letters*, vol. 5, No. 6, pp. 793-796, (2003).

Lebert, et al., "Trazodone in Fronto-Temporal Dementia," *Research and Practice in Alzheimer's Disease*, vol. 11, pp. 356-360, (2006).
Lee, et al. "Novel, Highly Potent, Selective 5-$HT_{2A}/D_2$ Receptor Antagonists as Potential Atypical Antipsychotics," *Bioorg. Med. Chem. Lett.*, vol. 13, pp. 767-770, (2003).
Li, et al., "Discovery of a Tetracyclic Quinoxaline Derivative as a Potent and Orally Active Multifunctional Drug Candidate for the Treatment of Neuropsychiatric and Neurological Disorders," *Journal of Medicinal Chemistry*, vol. 57, pp. 2670-2682, (2014).
Lieberman, et al., "ITI-007 for the Treatment of Schizophrenia: A 4-Week Randomized, Double-Blind, Controlled Trial," *Biol. Psychiatry*, vol. 79, No. 12, pp. 952-961, (2015).
Lin, et al., "Dosage and Duration of Antipsychotic Treatment in Demented Outpatients with Agitation or Psychosis," *Journal of the Formosan Medical Association*, vol. 114, pp. 147-153, (2015).
Lipschitz, et al., "Childhood Posttraumatic Stress Disorder: A Review of Neurobiologic Sequelae," *Psychiatric Annals Journal*, vol. 28, No. 8, pp. 452-457, (1998).
Lopez, et al., "Psychiatric Symptoms Vary with the Severity of Dementia in Probably Alzheimer's Disease," *J. Neuropsychiatry Clin. Neurosc.*, vol. 15, No. 3, pp. 346-353, (2003).
Louie, et al., "Palladium-Catalyzed Synthesis of Arylamines from Aryl Halides, Mechanistic Studies lead to Coupling in the Absence of Tin Reagents", *Tetrahedron Letters*, vol. 36, No. 21, pp. 3609-3612, (1995).
Lounkine, et al., "Formal Concept Analysis for the Identification of Molecular Fragment Combinations Specific for Active and Highly Potent Compounds," *J. Med. Chem.*, vol. 51, No. 17, pp. 5342-5348, (2008).
Madhusoodanan, S., et al., "Pharmacological Management of Behavioral Symptoms Associated with Dementia," *World J. Psychiatr.*, vol. 4, No. 4, pp. 72-79, (2014).
March, et al, *Advanced Organic Chemistry; Reactions, Mechanisms and Structures*, Fourth Edition, pp. 910-911, (1992).
Marcoux, et al., "A General Copper-catalyzed Synthesis of Diaryl Ethers," *J. Am. Chem. Soc.*, vol. 119, pp. 10539-10540, (1997).
Mohamed, et al., "Pharmacotherapy of PTSD in the U.S. Department of Veterans Affairs: Diagnostic- and Symptom-guided Drug Selection," *J. Clin. Psychiatry*, vol. 69, pp. 959-965, (2008).
Morgan, et al., "Acoustic Startle in Individuals With Posttraumatic Stress Disorder," *Psychiatric Annals Journal*, vol. 28, Issue 8, pp. 430-434, (1998).
Mulrooney, et al., "Recent Developments in Copper-catalyzed N-arylation with Aryl Halides," *Essay—University of Pennsylvania*, (2004).
Murakami, et al., "Fischer Indolization of Ethyl Pyruvate 2-[2-(Trifluoromethyl) phenyl]-phenylhydrazone and New Insight into the Mechanism of the Goldberg Reaction," *Chem. Pharm. Bull*, vol. 43, No. 8, pp. 1281-1286, (1995).
Nagai, et al., "Synthesis of 2,3,4,4a,5,9b-hexahydro-1H-pyrido[4,3-b] indole Derivatives and Their Central Nervous System Activities," *Journal of Medicinal Chemistry*, vol. 22, No. 6, pp. 677-683, (1979).
Newman, et al., "Solid-state Analysis of the Active Pharmaceutical Ingredient in Drug Products," *Drug Discovery Today*, vol. 8, No. 9, pp. 898-903, (2003).
Nihon rounen igaku zasshi, vol. 48, No. 3, pp. 195-204, (2011 nen). English translation only, 2 pages.
Pieniaszek, et al., "Moricizine Bioavailability via Simultaneous Dual, Stable Isotope Administration: Bioequivalence Implications," *J. Clin. Pharmacol.*, vol. 39, pp. 817-825, (1999).
Pond, et al., "Stereospecific Reduction of Haloperidol in Human Tissues," *Biochemical Pharmacology*, vol. 44, No. 5, pp. 867-871, (1992).
"Protection for the Amino Group," *Protective Groups in Organic Synthesis, Third Edition*, John Wiley & Sons, Inc., pp. 494-505, (1999).
PubChem, OPEN Chemistry Database, Compound Summary for CID-22036753, pp. 4, (2007), 12 pages.
Rackova, et al., "Free Radical Scavenging and Antioxidant Activities of Substituted Hexahydropyridoindoles. Quantitative Structure-Activity Relationships." *Journal of Medicinal Chemistry*, vol. 49, No. 8, pp. 2543-2548, (2006).

(56) References Cited

OTHER PUBLICATIONS

Rainer, M.K., "Risperidone Long-acting Injection: A Review of its Long Term Safety and Efficacy," *Neuropsychiatric Disease and Treatment*, vol. 4, No. 5, pp. 919-927, (2008).
Rye (Sleep Disorders and Parkinson's Disease, 2000, accessed online http://www.waparkinsons.org/edu_research/articles/Sleep_Disorders.html), 2 pages.
Sadighi, et al., "A Highly Active Palladium Catalyst System for the Arylation of Anilines," *Tetrahedron Letters*, vol. 39, pp. 5327-5330, (1998).
Savjani, et al., "Drug Solubility: Importance and Enhancement Techniques," *International Scholarly Research Network Pharmaceutics*, vol. 2012, pp. 1-10, (2012).
"Securities," *Bennett v. Alkermes, Inc.*, at http://securities.stanford.edu/filings-documents/1029/ALKS03-01/20031029_r01c_0312091.pdf (retrieved from the internet on Jun. 13, 2017), (2003).
Sigel, et al., "Tenary Complexes in Solution," *Inorganic Chemistry*, vol. 13, No. 2, pp. 462-465, (1974).
Singhal, et al., "Drug Polymorphism and Dosage Form Design: A Practical Perspective," *Advanced Drug Delivery Reviews*, vol. 56, pp. 335-347, (2004).
Skoog, et al., *Principles of Instrumental Analysis*, Fourth Edition, pp. 577, (1992).
Smith, et al., "Oxford Dictionary of Biochemistry and Molecular Biology", *Oxford University Press*, pp. 145, (1997).
Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.
Southwick, et al., "Neuroendocrine Alterations in Posttraumatic Stress Disorder," *Psychiatric Annals Journal*, vol. 28, No. 8, pp. 436-442, (1998).
Sugahara, et al., "A Facile Copper-Catalyzed Ullman Condensation: N-Arylation of Heterocyclic Compounds Containing an -NHCO-Moiety," *Chem. Pharm. Bull.*, vol. 45, No. 4, pp. 719-721, (1997).
Taragano, et al., "A Double-Blind, Randomized, Fixed-Dose Trial of Fluoxetine vs. Amitriptyline in the Treatment of Major Depression Complicating Alzheimer's Disease," *Psychosomatics*, vol. 38, No. 3, pp. 246-252, (1997).
Tariot, et al., "Memantine Treatment in Patients with Moderate to Severe Alzheimer Disease Already Receiving Donepezil: A Randomized Controlled Trail," *JAMA*, vol. 291, No. 3, pp. 317-324, (2004).
Tonn, G.R., et al., "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes," *Biological Mass Spectrometry*, vol. 22, pp. 633-642, (1993).
Wagaw, et al., "A Palladium-catalyzed Method for the Preparation of Indoles via the Fischer Indole Synthesis," *Journal of the American Chemical Society*, vol. 121, No. 44, pp. 10251-10263, (1999).
Weschules, et al., "Acetylcholinesterase Inhibitor and N-Methyl-D-Aspartic Acid Receptor Antagonist Use among Hospice Enrollees with a Primary Diagnosis of Dementia," *Journal of Palliative Medicine*, vol. 11, No. 5, pp. 738-745, (2008).
Wiese, M., "DSC Detection of Polymorphism in Pharmaceutical Anhdrous Dexamethasone Acetate," *TA Instruments*, TA302, pp. 1-4, (2002).
Wolen, R. L., "The Application of Stable Isotopes to Studies of Drug Bioavailability and Bioequivalence," *J. Clin. Pharmacol.*, vol. 26, pp. 419-424, (1986).
Wolfe, et al., "An Improved Catalyst System for Aromatic Carbon-nitrogen Bond Formation: The Possible Involvement of bis(phosphine) Palladium Complexes as Key Intermediates," *JACS*, vol. 118, pp. 7215-7216, (1996).
Wolfe, et al., "Intramolecular Palladium-catalyzed Aryl Amination and Aryl Amidation," *Tetrahedron*, vol. 52, No. 21, pp. 7525-7546, (1996).
Wolter, et al., "Synthesis of N-aryl Hydrazides by Copper-catalyzed Coupling of Hydrazides with Aryl Iodides," *Organic Letters*, vol. 3, No. 23, pp. 3803-3805, (2001).
Written Opinion of the International Searching Authority for International Application No. PCT/US2013/036514 dated Aug. 16, 2013, 4 pages.
Yamada, et al., "A Mild Copper-mediated Intramolecular Amination of Aryl Halides," *Synlett*, No. 2, pp. 231-234, (2002).
Yang, B.H., "The Development of Efficient Protocols for the Palladium-catalyzed Cyclization Reactions of Secondary Amides and Carbamates," *Organic Letters*, vol. 1, No. 1, pp. 35-37, (1999).
Yudofsky, et al., "Propranolol in the Treatment of Rage and Violent Behavior in Patients with Chronic Brain Syndromes," *Am. J. Psychiatry*, vol. 138, pp. 218-220, (1981).
Zhang, et al., "Highly Efficient Copper-catalyzed N-arylation of Alkylamines with Aryl Iodides Using Phosphoramidite as Ligand," *Catalysis Communications*, vol. 6, pp. 784-787, (2005).
Zhang, et al., "The Role of Serotonin 5-HT2A Receptors in Memory and Cognition," *Front. Pharmacol.*, vol. 6, No. 225, pp. 1-17, (2015); DOI: 10.3389/fphar.2015.00225.
Press Release, "Intra-Cellular Therapies Announces Additional Results from Phase I/II Clinical Trail for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
Harvey, et al., "Lumateperone Improves Negative Symptoms Related to Emotional Experience (Avolition) in Patient with Schizophrenia," Abstract presented at the American Society of Clinical Psychopharmacology (ASCP) Annual Meeting; May 29-Jun. 1, 2018; Miami, FL.
Lieberman, et al., "ITI-007 for the Treatment of Schizophrenia: A 4-Week Randomized, Double-Blind, Controlled Trial," *Biological Psychiatry*, 79:952-961 (2015).
Press Release, "Intra-Cellular Therapies Presents Data on Symptom Improvement by Lumateperone on Negative Symptoms, Depression, and Social Function in Patients with Schizophrenia at the American Society of Clinical Psychopharmacology (ASCP) Annual Meeting," Intra-Cellular Therapies, Press Release Date: May 31, 2018, (https://ir.intracellulartherapies.com/news-releases/news-release-details/intra-cellular-therapies-presents-data-symptom-improvement), accessed on Aug. 29, 2019.
Press Release, "Intra-Cellular Therapies Announces Positive Top-Line Results from a Phase 3 Trial of Lumateperone in Patient with Bipolar Depression," Intra-Cellular Therapies, Press Release Date: Jul. 8, 2019, (https://ir.intracellulartherapies.com/news-releases/news-release-details/intra-cellular-therapies-announces-positive-top-line-results-0), accessed on Aug. 29, 2019.
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.

\* cited by examiner

ORGANIC COMPOUNDS

This application is a continuation of U.S. patent application Ser. No. 15/301,912 filed on Oct. 4, 2016, which is a National Stage Entry under 35 U.S.C. § 371 of International Application No. PCT/US2015/024340, filed on Apr. 3, 2015, which claims priority to U.S. Provisional Application No. 61/975,610 filed on Apr. 4, 2014, the contents of each of which are hereby incorporated by reference in their entireties.

FIELD OF THE INVENTION

The invention relates to particular substituted heterocycle fused gamma-carbolines, in free, pharmaceutically acceptable salt and/or substantially pure form as described herein, pharmaceutical compositions thereof, and methods of use in the treatment of diseases involving 5-HT$_{2A}$ receptor, serotonin transporter (SERT) and/or pathways involving dopamine D$_1$/D$_2$ receptor signaling systems, e.g., diseases or disorders such as anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression and mood disorders associated with psychosis or Parkinson's disease; psychosis such as schizophrenia associated with depression; bipolar disorder; and other psychiatric and neurological conditions, as well as to combinations with other agents.

Psychosis, particularly schizophrenia, affects 1.1% of the population worldwide. This illness comprises three phases: prodromal phase, active phase and residual phase. Prodromal phase is an early phase wherein subclinical signs and symptoms are observed. These symptoms may include loss of interest in usual pursuits, withdrawal from friends and family members, confusion, trouble with concentration, feeling of listlessness and apathy. Active phase is characterized by exacerbations of positive symptoms such as delusions, hallucinations and suspiciousness. Residual phase is characterized by negative symptoms such as emotional withdrawal, passive social withdrawal, and stereotyped thinking; and general psychopathology symptoms including active social avoidance, anxiety, tension, and somatic concerns. Residual phase symptoms also are often accompanied by depression, cognitive dysfunction and insomnia. Collectively, these residual phase symptoms are not well-treated by many antipsychotic drugs currently available on the market and therefore are usually observed after the active phase symptoms have subsided after treatment. This phase of the illness is when patients would like to return to more productive and fulfilling lives, but since the residual negative symptoms and cognitive impairment are not properly treated, it frustrates the return to such a function. There remains an urgent need for anti-psychotic agent, which can treat not just the active or acute phase symptoms, but also the residual phase symptoms of psychosis, e.g., schizophrenia. In addition, there is a need for medications to treat these symptoms that are free from undesirable side effects caused by off-target interactions with histamine H1 and muscarinic acetylcholine receptor systems.

BACKGROUND OF THE INVENTION

Substituted heterocycle fused gamma-carbolines are known to be agonists or antagonists of 5-HT2 receptors, particularly 5-HT$_{2A}$ and 5-HT$_{2C}$ receptors, in treating central nervous system disorders. These compounds have been disclosed in U.S. Pat. Nos. 6,548,493; 7,238,690; 6,552,017; 6,713,471; 7,183,282; U.S. RE39680, and U.S. RE39679, as novel compounds useful for the treatment of disorders associated with 5-HT$_{2A}$ receptor modulation such as obesity, anxiety, depression, psychosis, schizophrenia, sleep disorders, sexual disorders migraine, conditions associated with cephalic pain, social phobias, gastrointestinal disorders such as dysfunction of the gastrointestinal tract motility, and obesity.

PCT/US08/03340 (WO 2008/112280) and U.S. application Ser. No. 10/786,935 disclose methods of making substituted heterocycle fused gamma-carbolines and uses of these gamma-carbolines as serotonin agonists and antagonists useful for the control and prevention of central nervous system disorders such as addictive behavior and sleep disorders.

WO/2009/145900 discloses use of particular substituted heterocycle fused gamma-carbolines for the treatment of a combination of psychosis and depressive disorders as well as sleep, depressive and/or mood disorders in patients with psychosis or Parkinson's disease. In addition to disorders associated with psychosis and/or depression, this patent application discloses and claims use of these compounds at a low dose to selectively antagonize 5-HT$_{2A}$ receptors without affecting or minimally affecting dopamine D$_2$ receptors, thereby useful for the treatment of sleep disorders without the side effects of the dopamine D$_2$ pathways or side effects of other pathways (e.g., GABA$_A$ receptors) associated with conventional sedative-hypnotic agents (e.g., benzodiazepines) including but not limited to the development of drug dependency, muscle hypotonia, weakness, headache, blurred vision, vertigo, nausea, vomiting, epigastric distress, diarrhea, joint pains, and chest pains.

Furthermore, it has been discovered that these substituted heterocycle fused gamma-carboline compounds are effective in treating not just acute symptoms, but also residual symptoms of psychosis. Therefore, methods of using these substituted heterocycle fused gamma-carboline compounds, either alone or as an adjunctive therapy for the treatment of residual symptoms of psychosis, particularly schizophrenia, were disclosed. See for example, application PCT/US2014/68443.

WO 2009/114181 discloses methods of preparing toluenesulfonic acid addition salt crystals of particular substituted heterocycle fused gamma-carbolines, e.g., toluenesulfonic acid addition salt of 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone.

WO 2011/133224 discloses prodrugs/metabolites of substituted heterocycle fused gamma-carboline for improved formulation, e.g., extended/controlled release formulation. This application discloses that heterocycle fused gamma-carboline N-substituted with a 4-fluorophenyl(4-hydroxy)butyl moiety are shown to have high selectivity for the serotonin transporter (SERT) relative to the heterocycle fused gamma-carboline containing 4-fluorophenylbutanone. The hydroxy group on these compounds, however, is inter-converted to and from the ketone within the plasma and the brain, allowing it to serve as a reservoir for the 4-fluorophenylbutanone drug. While substituted heterocycle fused gamma-carbolines and their uses are known, our inventors have surprisingly found that particular substituted heterocycle fused gamma-carbolines, while less active in in-vitro tests, are inter-converted between these less active compounds and the highly active ketone drug within the plasma and the brain. Our inventors have further provided prodrugs of particular substituted heterocycle fused gamma-carbolines that have altered pharmacokinetic profile, e.g., altered mechanisms and/or rate of absorption and distribution, and therefore may be useful for an improved formulation and/or for controlling the duration of the effect of the drug in the body (e.g., for sustained- or controlled release).

WO 2013/155505 discloses compounds which block the in vivo inter-conversion between the hydroxy and the ketone, by incorporating an alkyl substituent on the carbon bearing the hydroxyl group, thus yielding compounds which antagonize 5-HT$_{2A}$ receptors and also inhibit serotonin re-uptake transporter.

The major routes of metabolism of the compounds previously disclosed are N-demethylation catalyzed by CYP 3A4, and ketone reduction catalyzed by ketone reductase. N-dealkylation by cytochrome oxidase enzymes is known to occur via an initial oxidation of one or more of the carbon atoms alpha to the nitrogen atom. The family of enzymes that catalyze ketone reduction is large and varied, and the mechanism has not been absolutely elucidated. It is of interest that, mechanistically, ketone reduction may operate either by way of the enol tautomer of the ketone or the keto tautomer.

SUMMARY OF THE INVENTION

Without being bound by theory, the current invention provides compounds which partially limit metabolism of the ketone and/or the N-methyl substituent, by incorporating deuterium atoms in various locations. Due to the very similar properties of deuterium ($^2$H) atoms compared to normal hydrogen atoms ($^1$H), drug compounds in which deuterium is substituted for hydrogen are believed to generally have similar biological activity to the non-deuterated analog. Thus, the current invention provides compounds containing a trideuterated N-methyl, a mono- or di-deuterated methylene adjacent to the N-methyl, or a mono- or di-deuterated methylene adjacent to the ketone, or any combination of these deuterations. These novel compounds will antagonize 5-HT$_{2A}$ receptors, inhibit the serotonin re-uptake transporter, and modulate dopaminergic protein phosphorylation, in a like manner as to their natural hydrogen analogs, but will have an improved metabolic profile. Our inventors have shown that deuterations of some metabolically labile positions improves in vitro hepatic microsome stability, whereas deuteration of the 4-fluoro-phenyl ring (to yield a compound containing a 2,3,5,6-tetradeutero-4-fluoro ring) does not improve microsomal stability.

In the first aspect, the invention provides a compound of formula I:

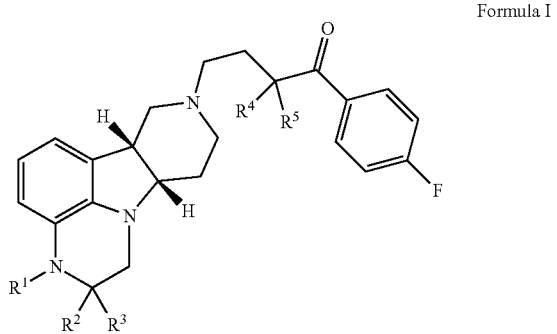

Formula I wherein:
R$^1$ is CH$_3$ or CD$_3$;
R$^2$ and R$^3$ are each independently H or D;
R$^4$ and R$^5$ are each independently H or D;
provided that R$^2$, R$^3$, R$^4$, and R$^5$ are not all H when R$^1$ is CH$_3$,
and wherein D is deuterium;
in free or salt form.

In a further embodiment of the first aspect, the invention provides the Compound of Formula I, as described in the following formulae:
1.1 the compound of Formula I, wherein R$^1$ is CD$_3$;
1.2 the compound of Formula I, wherein R$^2$ and R$^3$ are D;
1.3 the compound of Formula I, wherein R$^4$ and R$^5$ are D;
1.4 the compound of Formula I, wherein R$^1$ is CD$_3$ and R$^2$ and R$^3$ are both D;
1.5 the compound of Formula I, wherein R$^1$ is CD$_3$ and R$^4$ and R$^5$ are both D;
1.6 the compound of Formula I, wherein R$^2$ and R$^3$ and R$^4$ and R$^5$ are all D;
1.7 the compound of Formula I, wherein R$^1$ is CD$_3$, and R$^2$ and R$^3$ and R$^4$ and R$^5$ are all D;
1.8 the Compound of Formula I or any of 1-1.7, wherein the Compound is in substantially pure diastereomeric form (i.e., substantially free from other diastereomers);
1.9 the Compound of Formula I or any of 1-1.7, wherein the Compound has a diastereomeric excess of greater than 70%, preferably greater than 80%, more preferably greater than 90% and most preferably greater than 95%;
in free or salt form.

In a second aspect, the invention provides a compound of Formula II:

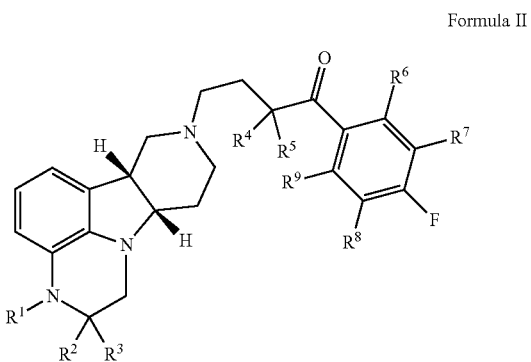

Formula II wherein R$^1$ through R$^5$ are as defined above in Formula I, and wherein R$^6$ to R$^9$ are each independently selected from H and D.

In a further embodiment of the first aspect, the invention provides a compound of Formula I, in free or salt form as described in the following formulae:
4.1 the Compound of Formula I or any of 1-1.9, wherein the salt is selected from a group consisting of hydrochloric, hydrobromic, sulfuric, sulfamic, phosphoric, nitric, acetic, propionic, succinic, glycolic, stearic, lactic, malic, tartaric, citric, ascorbic, palmoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like;
4.2 the Compound of Formula I or formula 4.1, wherein the salt is fumaric acid addition salt;

4.3 the Compound of Formula I or formula 4.1, wherein the salt is phosphoric acid addition salt;

4.4 the Compound of Formula I or formula 4.1, wherein the salt is a toluenesulfonic acid addition salt.

In a second aspect, the invention provides a pharmaceutical composition comprising the compound of formula I, or any of 1-1.9 or 4.1-4.4 (the Compounds of the Invention), in free or pharmaceutically acceptable salt form, in admixture with a pharmaceutically acceptable diluent or carrier, e.g. to provide immediate release or to provide sustained or delayed release.

In a further embodiment of the second aspect, the Pharmaceutical Composition of the Invention is for a sustained or delayed release, e.g., a depot formulation. In one embodiment, the depot formulation comprises the Compounds of the Invention in a polymeric matrix. In another embodiment, the Compounds of the Invention are dispersed or dissolved within the polymeric matrix. In a further embodiment, the polymeric matrix comprises standard polymers used in depot formulations such as polymers selected from a polyester of a hydroxy fatty acid and derivatives thereof, or a polymer of an alkyl alpha-cyanoacrylate, a polyalkylene oxalate, a poly(ortho ester), a polycarbonate, a polyorthocarbonate, a poly(amino acid), a hyaluronic acid ester, and mixtures thereof. In a further embodiment, the polymer is selected from a group consisting of polylactide, poly d,l-lactide, poly glycolide, PLGA 50:50, PLGA 75:25, PLGA 85:15 and PLGA 90:10 polymer. In another embodiment, the polymer is selected from poly(glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. In a particular embodiment, the polymeric matrix comprises poly (d,l-lactide-co-glycolide). Any of the Compositions hereinbefore described may be a pharmaceutical composition wherein said composition is in admixture with a pharmaceutically acceptable diluent or carrier.

The (Pharmaceutical) depot formulations as hereinbefore described are particularly useful for sustained or delayed release, wherein the Compounds of the Invention are released upon degradation of the polymeric matrix. These Compositions may be formulated for controlled- and/or sustained-release of the Compounds of the Invention (e.g., as a depot composition) over a period of up to 180 days, e.g., from about 14 to about 30 to about 180 days. For example, the polymeric matrix may degrade and release the Compounds of the Invention over a period of about 30, about 60 or about 90 days. In another example, the polymeric matrix may degrade and release the Compounds of the Invention over a period of about 120, or about 180 days.

In still another further embodiment, the Pharmaceutical Compositions of the Invention, particularly the depot compositions of the Invention, are formulated for administration by injection.

In the third aspect, the invention provides the Compounds of the Invention as hereinbefore described in an oral sustained or delayed release formulation. For example, the invention provides an osmotic controlled release oral delivery system (OROS) for delivery of the Compounds of the Invention, e.g. analogous to the systems described in WO 2000/35419 and EP 1 539 115 (U.S. Pub. No. 2009/0202631), the contents of each of which applications are incorporated by reference in their entirety. Therefore in one embodiment of this aspect, the invention provides a pharmaceutical composition or device comprising (a) a gelatin capsule containing a Compound of the Invention in free or pharmaceutically acceptable salt form or a Pharmaceutical Composition of the Invention, as hereinbefore described; (b) a multilayer wall superposed on the gelatin capsule comprising, in outward order from the capsule: (i) a barrier layer, (ii) an expandable layer, and (iii) a semipermeable layer; and (c) and orifice formed or formable through the wall. (Composition P.1)

In another embodiment of this aspect, the invention provides a composition comprising a gelatin capsule containing a liquid, the Compounds of the Invention in free or pharmaceutically acceptable salt form or a Pharmaceutical Composition of the Invention as hereinbefore described, the gelatin capsule being surrounded by a composite wall comprising a barrier layer contacting the external surface of the gelatin capsule, an expandable layer contacting the barrier layer, a semi-permeable layer encompassing the expandable layer, and an exit orifice formed or formable in the wall. (Composition P.2)

In still another embodiment of the third aspect, the invention provides a composition comprising a gelatin capsule containing a liquid, the Compound of the Invention in free or pharmaceutically acceptable salt form or a Pharmaceutical Composition of the Invention as hereinbefore described, the gelatin capsule being surrounded by a composite wall comprising a barrier layer contacting the external surface of the gelatin capsule, an expandable layer contacting the barrier layer, a semipermeable layer encompassing the expandable layer, and an exit orifice formed or formable in the wall, wherein the bather layer forms a seal between the expandable layer and the environment at the exit orifice. (Composition P.3)

In still another embodiment of the third aspect, the invention provides a composition comprising a gelatin capsule containing a liquid, the Compound of the Invention in free or pharmaceutically acceptable salt form or a Pharmaceutical Composition of the Invention as hereinbefore described, the gelatin capsule being surrounded by a barrier layer contacting the external surface of the gelatin capsule, an expandable layer contacting a portion of the barrier layer, a semi-permeable layer encompassing at least the expandable layer, and an exit orifice formed or formable in the dosage form extending from the external surface of the gelatin capsule to the environment of use. (Composition P.4). The expandable layer may be formed in one or more discrete sections, such as for example, two sections located on opposing sides or ends of the gelatin capsule.

In a particular embodiment of the third aspect, the Compound of the Inventions in the Osmotic-controlled Release Oral delivery System (i.e., in Composition P.1-P.4) are in a liquid formulation, which formulation may be neat, liquid active agent, liquid active agent in a solution, suspension, emulsion or self-emulsifying composition or the like.

Further information on Osmotic-controlled Release Oral delivery System composition including characteristics of the gelatin capsule, barrier layer, an expandable layer, a semi-permeable layer; and orifice may be found in WO 2000/35419, the contents of which are incorporated by reference in their entirety. Other Osmotic-controlled Release Oral delivery System for the Compound or the Pharmaceutical Composition of the Invention may be found in EP 1 539 115 (U.S. Pub. No. 2009/0202631), the contents of which are incorporated by reference in their entirety.

Therefore, in another embodiment of the third aspect, the invention provides a composition or device comprising (a)

two or more layers, said two or more layers comprising a first layer and a second layer, said first layer comprises the Compound of the Invention, in free or pharmaceutically acceptable salt form, or a Pharmaceutical Composition as herein before described said second layer comprises a polymer; (b) an outer wall surrounding said two or more layers; and (c) an orifice in said outer wall. (Composition P.5)

Composition P.5 preferably utilizes a semi-permeable membrane surrounding a three-layer-core: in these embodiments the first layer is referred to as a first drug layer and contains low amounts of drug (e.g., the Compounds of the Invention) and an osmotic agent such as salt, the middle layer referred to as the second drug layer contains higher amounts of drug, excipients and no salt; and the third layer referred to as the push layer contains osmotic agents and no drug. At least one orifice is drilled through the membrane on the first drug layer end of the capsule-shaped tablet. (Composition P.6)

Composition P.5 or P.6 may comprise a membrane defining a compartment, the membrane surrounding an inner protective subcoat, at least one exit orifice formed or formable therein and at least a portion of the membrane being semi-permeable; an expandable layer located within the compartment remote from the exit orifice and in fluid communication with the semi-permeable portion of the membrane; a first drug layer located adjacent the exit orifice; and a second drug layer located within the compartment between the first drug layer and the expandable layer, the drug layers comprising the Compound of the Invention in free or pharmaceutically acceptable salt thereof. Depending upon the relative viscosity of the first drug layer and second drug layer, different release profiles are obtained. It is imperative to identify the optimum viscosity for each layer. In the present invention, viscosity is modulated by addition of salt, sodium chloride. The delivery profile from the core is dependent on the weight, formulation and thickness of each of the drug layers. (Composition P.7)

In a particular embodiment, the invention provides Composition P.7 wherein the first drug layer comprising salt and the second drug layer containing no salt. Composition P.5-P.7 may optionally comprise a flow-promoting layer between the membrane and the drug layers. Compositions P.1-P.7 will generally be referred to as Osmotic-controlled Release Oral delivery System Composition.

In the fourth aspect, the invention provides a method (Method I) for the treatment or prophylaxis of a central nervous system disorder, comprising administering to a patient in need thereof, a Compound of Formula I or any of formulae 1-1.9, in free or pharmaceutically acceptable salt form as described in any of 4.1-4.4, or a pharmaceutical composition as hereinbefore described.

In a further embodiment of the fourth aspect, the invention provides Method I wherein the method is further as described in the following formulae:

7.1 Method I, wherein the central nervous system disorder is one or more disorders associated with dementia, e.g., disorders associated with mild cognition impairment and dementing illnesses including senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoffs syndrome, cortico-basal degenerations and prion disease, autism and attention deficit hyperactivity disorder, as disclosed in WO 2013/155506, the contents of which is incorporated herein by reference in its entirety;

7.2 Method I or 7.1, wherein the disorders associated with dementia is selected from the group consisting of (1) behavioral or mood disorders such as agitation/irritation, aggressive/assaultive behavior, anger, physical or emotional outbursts; (2) psychosis; (3) depression; and (4) sleep disorders;

7.3 Method I or 7.1, wherein the central nervous system disorder is agitation/irritation, aggressive/assaultive behavior, anger, physical or emotional outbursts, as disclosed in WO 2013/155504, the contents of which is incorporated herein by reference in its entirety;

7.4 Method I, wherein the central nervous system disorder is a disorder selected from a group consisting of obesity, anxiety, depression (for example refractory depression and major depressive disorder (MDD)), psychosis, schizophrenia, sleep disorders (particularly sleep disorders associated with schizophrenia and other psychiatric and neurological diseases), sexual disorders, migraine, conditions associated with cephalic pain, social phobias, agitation in dementia (e.g., agitation in Alzheimer's disease), agitation in autism and related autistic disorders, and gastrointestinal disorders such as dysfunction of the gastrointestinal tract motility;

7.5 Method I or any of 7.1-7.4, wherein the central nervous system disorder is a disorder involving serotonin 5-HT$_{2A}$, dopamine D$_1$/D$_2$ receptor system and/or serotonin reuptake transporter (SERT) pathways as similarly described in WO/2009/145900, the contents of which are herein incorporated by reference in their entirety;

7.6 Method I or any of Formulae 7.1-7.5, wherein the central nervous system disorder is a disorder involving serotonin reuptake transporter (SERT) pathways;

7.7 Method I or any of Formulae 7.1-7.6, wherein the central nervous system disorder is a disorder selected from the following: (i) psychosis, e.g., schizophrenia, in a patient suffering from depression; (2) depression in a patient suffering from psychosis, e.g., schizophrenia; (3) mood disorders associated with psychosis, e.g., schizophrenia or Parkinson's disease; and (4) sleep disorders associated with psychosis, e.g., schizophrenia or Parkinson's disease; (5) depression; (6) anxiety; (7) post-traumatic stress disorder; or (8) impulse control disorder, e.g., intermittent explosive disorder;

7.8 Method I or any of Formulae 7.1-7.7, wherein the central nervous system disorder is psychosis, e.g., schizophrenia and said patient is a patient suffering from depression;

7.9 Method I or any of Formulae 7.1-7.8, wherein said patient is unable to tolerate the side effects of convention antipsychotic drugs, e.g., chlorpromazine, haloperidol, droperidol, fluphenazine, loxapine, mesoridazine, molindone, perphenazine, pimozide, prochlorperazine, promazine, thioridazine, thiothixene, trifluoperazine, clozapine, aripiprazole, olanzapine, quetiapine, risperidone and ziprasidone;

7.10 Method I or any of Formulae 7.1-7.9, wherein said patient is unable to tolerate the side effects of convention antipsychotic drugs, e.g., haloperidol, aripiprazole, clozapine, olanzapine, quetiapine, risperidone, and ziprasidone;

7.11 Method I or any of Formulae 7.1-7.10, wherein said disorder is depression and said patient is a patient suffering from psychosis, e.g., schizophrenia, or Parkinson's disease;

7.12 Method I or any of Formulae 7.1-7.6, wherein said disorder is sleep disorder and said patient is suffering from depression;

7.13 Method I or any of 7.1-7.6, wherein said one or more disorders is sleep disorder and said patient is suffering from psychosis, e.g., schizophrenia;

7.14 Method I or any of 7.1-7.6, wherein said one or more disorders is sleep disorder and said patient is suffering from Parkinson's disease;

7.15 Method I or any of 7.1-7.6, wherein said one or more disorders is sleep disorder and said patient is suffering from depression and psychosis, e.g., schizophrenia, or Parkinson's disease;

7.16 Method I or any of 7.1-7.6, wherein the central nervous system disorder is residual symptoms of psychosis, for example, schizophrenia (e.g., residual subtype), delusional disorder (e.g., somatic type), major depression with psychosis, bipolar disorder with psychotic symptoms, brief psychotic disorder, schizophreniform disorder, schizoaffective disorder or psychosis caused by a medical condition or substance use. Preferably, the patient is suffering from residual symptoms of schizophrenia;

7.17 Method I or any of 7.1-7.6, wherein the residual phase symptoms include: negative symptoms such as blunted affect, emotional withdrawal, poor rapport, passive or apathetic social withdrawal, difficulty in abstract thinking, lack of spontaneity and flow of conversation and stereotyped thinking; general psychopathology symptoms such as somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance; cognitive impairment and sleep disorders (e.g., insomnia);

7.18 Any of the foregoing methods, wherein the effective amount is 1 mg-1000 mg, preferably 2.5 mg-50 mg, still preferably 1-40 mg, e.g., 1-10 mg, e.g., 10 mg, 20 mg, greater 20 mg, e.g., 30 mg, 40 mg;

7.19 Any of the foregoing methods, wherein the effective amount is 1 mg-100 mg per day, preferably 2.5 mg-50 mg per day, still preferably 1-40 mg/day, e.g., 1-10 mg/day, e.g., 10 mg/day, 20 mg/day, greater 20 mg/day, e.g., 30 mg/day, 40 mg/day;

7.20 Any of the foregoing methods wherein a condition to be treated is dyskinesia, e.g. in a patient receiving dopaminergic medications, e.g., medications selected from levodopa and levodopa adjuncts (carbidopa, COMT inhibitors, MAO-B inhibitors), dopamine agonists, and anticholinergics, e.g., levodopa;

7.21 Any of the foregoing methods wherein the patient suffers from Parkinson's disease;

7.22 Any of the foregoing methods wherein the patient does not respond to a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AIJS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Normud);

7.23 Any of the foregoing methods wherein the patients is also receiving a selective serotonin re-uptake inhibitor, e.g. selected from one or more of citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox); indalpine (Upstene); paroxetine (Paxil, Seroxat, Sereupin, Aropax, Deroxat, Divarius, Rexetin, Xetanor, Paroxat, Loxamine, Deparoc); sertraline (Zoloft, Lustral, Serlain, Asentra); vilazodone (Viibryd); or zimelidine (Zelmid, Noimud);

7.24 Any of the foregoing methods wherein the patients is suffering from autistic spectrum disorder, e.g., autism or Asperger Syndrome;

7.25 Any of the foregoing methods wherein the patients is suffering from dementia, e.g., disorders associated with mild cognition impairment and dementing illnesses including senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, cortico-basal degenerations and prion disease, autism and attention deficit hyperactivity disorder;

7.26 Any of the foregoing methods wherein the patient is also receiving a cholinesterase inhibitor (e.g., acetylcholinesterase inhibitor) or an N-Methyl D-Aspartate (NMDA) receptor antagonist, in free or phamiaceutically acceptable salt form;

7.27 Method 7.26, wherein the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form;

7.28 Method 7.26, wherein the cholinesterase inhibitor (e.g., acetylcholinesterase inhibitor) is donepezil in free or pharmaceutically acceptable salt form;

7.29 Method 7.26, wherein the NMDA receptor antagonist is memantine in free or pharmaceutically acceptable salt form;

7.30 Any of the foregoing methods further comprising administering one or more other therapeutic agents such as additional antipsychotic agents and/or anti-depressive agents and/or hypnotic agents;

7.31 Method 7.30, wherein the one or more other therapeutic agents are selected from anti-depressive agents such as compounds that modulate GABA activity (e.g., enhances the activity and facilitates GABA transmission), a GABA-B agonist, a 5-HT modulator (e.g., a 5-HT1A agonist, a 5-HT2A antagonist, a 5-HT2A inverse agonist, etc.), a melatonin agonist, an ion channel modulator (e.g., blocker), a serotonin-2 antagonist/reuptake inhibitor (SARIs), an orexin receptor antagonist, an H3 agonist, a noradrenergic antagonist, a galanin agonist, a CRH antagonist, human growth hormone, a growth hormone agonist, estrogen, an estrogen agonist, a neurokinin-1 drug; and antipsychotic agents, e.g., atypical antipsychotic agents, in free or pharmaceutically acceptable salt form;

7.32 Method 7.30 or 7.31, wherein the one or more other therapeutic agents are antipsychotic agents, e.g., chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone, paliperidone, asenapine, lurasidone, iloperidone, cariprazine, amisulpride, zotepine, sertindole, wherein the one or more other therapeutic agents are administered as an adjunct to the compound of Formula I or the compound of Formula I is an adjunct to the one or more other therapeutic agents.

In a particular embodiment of the fourth aspect, the invention provides a method (Method $I_P$) for the treatment or prophylaxis of a central nervous system disorder as hereinbefore described, comprising administering to a patient in need thereof:

7.4P a compound of Formula I or any of formulae 1-1.9, in free or (pharmaceutically acceptable) salt form as described in any of 4.1-4.4;

7.8P a Pharmaceutical or Depot Composition as hereinbefore described; or 7.11P Osmotic-controlled Release Oral delivery System Composition as hereinbefore described.

In a further embodiment of the fourth aspect, the invention provides Method $I_P$, wherein the method is further described in any one of formulae 7.1-7.32.

In a particular embodiment of the fourth aspect, the invention provides Method I, $I_P$, or any of 7.1-7.32, wherein the disorder is schizophrenia or sleep disorder.

In a particular embodiment of the fourth aspect, the invention provides Method I, $I_P$, or any of 7.1-7.32, wherein the disorder is depression or anxiety.

In a particular embodiment of the fourth aspect, the invention provides Method I, $I_P$, or any of 7.1-7.32, wherein the disorder is post-traumatic stress disorder or an impulse control disorder, e.g., intermittent explosive disorder.

In a particular embodiment of the fourth aspect, the invention provides Method I, $I_P$, or any of 7.1-7.32, wherein the disorder is post-traumatic stress disorder or an impulse control disorder, e.g., intermittent explosive disorder in a patient suffering from dementia, e.g., senile dementia, Alzheimer's disease, Pick's disease, fronto-temporal dementia, parasupranuclear palsy, dementia with Lewy bodies, vascular dementia, Huntington's disease, Parkinson's disease, multiple sclerosis, amyotrophic lateral sclerosis, Down syndrome, elderly depression, Wernicke-Korsakoff's syndrome, cortico-basal degenerations, prion disease, autism and/or attention deficit hyperactivity disorder.

In still another embodiment of the fourth aspect, the invention provides Method I, $I_P$, or any of 7.1-7.32, wherein the Depot Composition of the Invention is administered for controlled- and/or sustained-release of the Compounds of the Invention over a period of from about 14 days, about 30 to about 180 days, preferably over the period of about 30, about 60 or about 90 days. Controlled- and/or sustained-release is particularly useful for circumventing premature discontinuation of therapy, particularly for antipsychotic drug therapy where non-compliance or non-adherence to medication regimes is a common occurrence.

In the fifth aspect, the invention provides a method (Method II) for the prophylaxis or treatment one or more sleep disorders, agitation, aggressive behaviors, post-traumatic stress disorder and/or impulse control disorder, e.g., intermittent explosive disorder, comprising administering to a patient in need thereof a compound as described in the following formulae:

8.1 a compound of Formula I or any of formulae 1-1.9, in free or (pharmaceutically acceptable) salt form as described in any of 4.1-4.4;

8.2 a Pharmaceutical or Depot Composition as hereinbefore described;

8.3 Osmotic-controlled Release Oral delivery System Composition as hereinbefore described.

In one embodiment of the fifth aspect, the invention provides Method II or any of 8.1-8.3, wherein the disorder is sleep disorders. In another embodiment of the fifth aspect, the invention provides Method II, wherein the disorder is agitation, aggressive behaviors, post-traumatic stress disorder and/or impulse control disorder, e.g., intermittent explosive disorder.

In a further embodiment of the fifth aspect, the invention provides Method II, 8.1-8.3, wherein the sleep disorder includes sleep maintenance insomnia, frequent awakenings, and waking up feeling unrefreshed;

8.11 Any of the foregoing methods, wherein the sleep disorder is sleep maintenance insomnia;

8.12 Any of the foregoing methods, wherein the effective amount is 1 mg-10 mg per day, e.g., 1-5 mg, preferably 2.5-5 mg, per day, still preferably 10 mg per day;

8.13 Any of the foregoing methods, wherein the effective amount is 2.5 mg or 5 mg, per day or 10 mg per day;

8.14 Any of the foregoing methods wherein the sleep disorder is in a patient suffering from or at risk of dyskinesia, e.g., a patient receiving dopaminergic medications, e.g., selected from levodopa and levodopa adjuncts (carbidopa, COMT inhibitors, MAO-B inhibitors), dopamine agonists, and anticholinergics, e.g., receiving levodopa;

8.15 Any of the foregoing methods wherein the patient suffers from Parkinson's disease.

The Compounds of the Invention provide effective treatment of 5-$HT_{2A}$, SERT and/or $D_2$ receptor related disorders without or with minimal extrapyramidal side effects as similarly disclosed and claimed in WO 2009/145900, the contents of which are incorporated by reference in their entirety. Therefore, the Compounds of the Invention, the Pharmaceutical Compositions of the Invention or the Depot Compositions of the Invention may be used in combination with a second therapeutic agent, particularly at lower dosages than when the individual agents are used as a monotherapy so as to enhance the therapeutic activities of the combined agents without causing the undesirable side effects commonly occur in conventional monotherapy. Therefore, the Compounds of the Invention may be simultaneously, sequentially, or contemporaneously administered with other anti-depressant, anti-psychotic, other hypnotic agents, and/or agents use to treat Parkinson's disease or mood disorders or dementia. In another example, side effects may be reduced or minimized by administering a Compound of the Invention in combination with one or more second therapeutic agents in free or salt form, wherein the dosages of (i) the second therapeutic agent(s) or (ii) both Compound of the Invention and the second therapeutic agent, are lower than if the agent/compound are administered as a monotherapy. In a particular embodiment, the Compounds of the Invention are useful to treat dyskinesia in a patient receiving dopaminergic medications, e.g., selected from levodopa and levodopa adjuncts (carbidopa, COMT inhibitors, MAO-B inhibitors), dopamine agonists, and anticholinergics, e.g., such as are used in the treatment of Parkinson's disease.

Therefore, in the sixth aspect, the current invention provides Method I or I$_P$, e.g., or any of formulae 7.1-7.32, or Method II or any of 8.1-8.15, further comprises one or more therapeutic agents selected from compounds that modulate GABA activity (e.g., enhances the activity and facilitates GABA transmission), a GABA-B agonist, a 5-HT modulator (e.g., a 5-HT$_{1A}$ agonist, a 5-HT$_{2A}$ antagonist, a 5-HT$_{2A}$ inverse agonist, etc.), a melatonin agonist, an ion channel modulator (e.g., blocker), a serotonin-2 antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method I-A and II-A respectively).

In another embodiment of the sixth aspect, Method I-A and II-A, Method I, Method I$_P$, e.g., or any of formulae 7.1-7.32, or Method II or any of 8.1-8.15, further comprises one or more therapeutic agents selected from a cholinesterase inhibitor (e.g., acetylcholinesterase inhibitor) or an N-Methyl D-Aspartate (NMDA) receptor antagonist, in free or pharmaceutically acceptable salt form. In a specific embodiment, the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form. In a further embodiment, the cholinesterase inhibitor (e.g., acetylcholinesterase inhibitor) is donepezil in free or pharmaceutically acceptable salt form. In another embodiment, the NMDA receptor antagonist is memantine in free or pharmaceutically acceptable salt form.

In a further embodiment of the sixth aspect, the invention provides Method I-A or II-A as follows, further comprising one or more therapeutic agents.

9.1 Method I-A or II-A, wherein the therapeutic agent(s) is compounds that modulate GABA activity (e.g., enhances the activity and facilitates GABA transmission);

9.2 Method I-A or II-A or 9.1, wherein the GABA compound is selected from a group consisting of one or more of doxepin, alprazolam, bromazepam, clobazam, clonazepam, clorazepate, diazepam, flunitrazepam, fiurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals) and estazolam;

9.3 Method I-A or II-A, wherein the therapeutic agent is an additional 5HT$_{2A}$ antagonist;

9.4 Method I-A or II-A or 9.3, wherein said additional 5HT$_{2A}$ antagonist is selected from one or more of ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), and AVE8488 (Sanofi-Aventis, France); Method I-A or II-A, 9.3 or 9.4 additionally selected from pimavanserin (ACP-103) and pizotifen;

9.5 Method I-A or II-A, wherein the therapeutic agent is a melatonin agonist;

9.6 Method I-A or II-A or 9.5, wherein the melatonin agonist is selected from a group consisting of one or more of melatonin, ramelteon (ROZEREM®, Takeda Pharmaceuticals, Japan), VEC-162 (Vanda Pharmaceuticals, Rockville, Md.), PD-6735 (Phase II Discovery) and agomelatine;

9.7 Method I-A or II-A, wherein the therapeutic agent is an ion channel blocker;

9.8 Method I-A or II-A or 9.7, wherein said ion channel blocker is one or more of lamotrigine, gabapentin and pregabalin.

9.9 Method I-A or II-A, wherein the therapeutic agent is an orexin receptor antagonist;

9.10 Method I-A or II-A or 9.9, wherein the orexin receptor antagonist is selected from a group consisting of orexin, a 1,3-biarylurea, SB-334867-a (GlaxoSmithKline, UK), GW649868 (GlaxoSmithKline) and a benzamide derivative;

9.11 Method I-A or II-A, wherein the therapeutic agent is the serotonin-2 antagonist/reuptake inhibitor (SARI);

9.12 Method I-A or II-A or 9.11, wherein the serotonin-2 antagonist/reuptake inhibitor (SARI) is selected from a group consisting of one or more Org 50081 (Organon—Netherlands), ritanserin, nefazodone, serzone and trazodone;

9.13 Method I-A or II-A, wherein the therapeutic agent is the 5HT1a agonist;

9.14 Method I-A or II-A or 9.13, wherein the 5HT$_{1a}$ agonist is selected from a group consisting of one or more of repinotan, sarizotan, eptapirone, buspirone and MN-305 (MediciNova, San Diego, Calif.);

9.15 Method I-A or II-A, wherein the therapeutic agent is the neurokinin-1 drug;

9.16 Method I-A or II-A or 9.15, wherein the neurokinin-1 drug is Casopitant (GlaxoSmithKline);

9.17 Method I-A or II-A, wherein the therapeutic agent is an antipsychotic agent;

9.18 Method I-A or II-A or 9.17, wherein the antipsychotic agent is selected from a group consisting of chlorpromazine, haloperidol, droperidol, fluphenazine, loxapine, mesoridazine, molindone, perphenazine, pimozide, prochlorperazine promazine, thioridazine, thiothixene, trifluoperazine, clozapine, aripiprazole, olanzapine, quetiapine, risperidone, ziprasidone and paliperidone;

9.19 Method I-A or II-A, wherein the therapeutic agent is an anti-depressant;

9.20 Method I-A or II-A or 9.19, wherein the anti-depressant is selected from amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, and venlafaxine;

9.21 Method I-A or II-A, 9.17 or 9.18, wherein the antipsychotic agent is an atypical antipsychotic agent;

9.22 Method I-A or II-A, or any of 9.17-9.21, wherein the atypical antipsychotic agent is selected from a group consisting of clozapine, aripiprazole, olanzapine, quetiapine, risperidone, ziprasidone, and paliperidone;

9.23 Method I-A or II-A, wherein the therapeutic agent is selected from any of methods 9.1-9.22, e.g., selected from a group consisting of modafinil, armodafinil, doxepin, alprazolam, bromazepam, clobazam, clonazepam, clorazepate, diazepam, flunitrazepam, flurazepam, lorazepam, midazolam, nitrazepam, oxazepam, temazapam, triazolam, indiplon, zopiclone, eszopiclone, zaleplon, Zolpidem, gabaxadol, vigabatrin, tiagabine, EVT 201 (Evotec Pharmaceuticals), estazolam, ketanserin, risperidone, eplivanserin, volinanserin (Sanofi-Aventis, France), pruvanserin, MDL 100907 (Sanofi-Aventis, France), HY 10275 (Eli Lilly), APD 125 (Arena Pharmaceuticals, San Diego, Calif.), AVE8488 (Sanofi-Aventis, France), repinotan, sarizotan, eptapirone, buspirone, MN-305 (MediciNova, San Diego, Calif.), melatonin, ramelteon (ROZEREM®, Takeda Pharmaceuticals, Japan), VEC-162 (Vanda Pharmaceuticals, Rockville, Md.), PD-6735 (Phase II Discovery), agomelatine, lamotrigine, gabapentin, pregabalin, orexin, a 1,3-biarylurea, SB-334867-a (GlaxoSmithKline, UK), GW649868 (GlaxoSmithKline), a benzamide derivative, Org 50081 (Organon-Netherlands), ritanserin, nefazodone, serzone, trazodone, Casopitant (GlaxoSmithKline), amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, venlafaxine, chlorpromazine, haloperidol, droperidol, fluphenazine, loxapine, mesoridazine molindone, perphenazine, pimozide, prochlorperazine promazine, thioridazine, thiothixene, trifluoperazine, clozapine, aripiprazole, olanzapine, quetiapine, risperidone, ziprasidone and paliperidone; In addition to the therapeutic agents listed herewith, Method I-A or II-A, is further selected from pimavanserin (ACP-103) and pizotifen;

9.24 Method I-A or II-A wherein the therapeutic agent is an H3 agonist;

9.25 Method I-A or II-A, wherein the therapeutic agent is an H3 antagonist;

9.26 Method I-A or II-A, wherein the therapeutic agent is a noradrenergic agonist or antagonist;

9.27 Method I-A or II-A, wherein the therapeutic agent is a galanin agonist;

9.28 Method I-A or II-A, wherein the therapeutic agent is a CRH antagonist;

9.29 Method I-A or II-A, wherein the therapeutic agent is a human growth hormone;

9.30 Method I-A or II-A, wherein the therapeutic agent is a growth hormone agonist;

9.31 Method I-A or II-A, wherein the therapeutic agent is estrogen;

9.32 Method I-A or II-A, wherein the therapeutic agent is an estrogen agonist;

9.33 Method I-A or II-A, wherein the therapeutic agent is a neurokinin-1 drug;

9.34 Method I-A or II-A, wherein a therapeutic agent is combined with compounds of Formula (I) and the therapeutic agent is an anti-Parkinson agent such as L-dopa, co-careldopa, duodopa, stalova, Symmetrel, benzotropine, biperiden, bromocryiptine, entacapone, pergolide, pramipexole, procyclidine, ropinirole, selegiline and tolcapone;

9.35 Method I-A or II-A, wherein compounds of Formula (I) may be used to treat sleep disorders, depression, psychosis, or any combinations thereof, in patients suffering from the listed diseases and/or Parkinson's disease;

9.36 Method I-A or II-A, wherein the disorder is selected from at least one or more of psychosis, e.g., schizophrenia, depression, mood disorders, sleep disorders (e.g., sleep maintenance and/or sleep onset) or any combination of disorders thereof;

9.37 Any of the foregoing methods wherein the disorder is sleep disorder;

9.38 Any of the foregoing methods, wherein the disorder is sleep disorder associated with psychosis, e.g., schizophrenia or Parkinson's disease; in free or pharmaceutically acceptable salt form.

In another embodiment of the sixth aspect, the current invention provides Method $I_P$ or Method II as hereinbefore described, further comprises one or more therapeutic agents selected from compounds that modulate GABA activity (e.g., enhances the activity and facilitates GABA transmission), a GABA-B agonist, a 5-HT modulator (e.g., a 5-$HT_{1A}$ agonist, a 5-$HT_{2A}$ antagonist, a 5-$HT_{2A}$ inverse agonist, etc.), a melatonin agonist, an ion channel modulator (e.g., blocker), a serotonin-2 antagonist/reuptake inhibitor (SARIs), an orexin receptor antagonist, an H3 agonist or antagonist, a noradrenergic agonist or antagonist, a galanin agonist, a CRH antagonist, human growth hormone, a growth hormone agonist, estrogen, an estrogen agonist, a neurokinin-1 drug, an anti-depressant, and an antipsychotic agent, e.g., an atypical antipsychotic agent, in free or pharmaceutically acceptable salt form (Method $I_P$-A and II-A respectively). In a further embodiment of this aspect, the invention provides Method $I_P$-A or 11-A as similarly described in any one of formulae 9.1-9.38.

In still another embodiment of the sixth aspect, Method $I_P$ or Method II as hereinbefore described further comprises one or more therapeutic agents selected from a cholinesterase inhibitor (e.g., acetylcholinesterase inhibitor) or an N-Methyl D-Aspartate (NMDA) receptor antagonist, in free or pharmaceutically acceptable salt form. In a specific embodiment, the cholinesterase inhibitor (e.g., acetylcholinesterase inhibitor) is selected from the group consisting of Tacrine, rivastigmine (Exelon), donepezil (Aricept), and galantamine (Razadyne, formerly called Reminyl)) in free or pharmaceutically acceptable salt form. In a further embodiment, the cholinesterase inhibitor (e.g., acetylcholinesterase inhibitor) is donepezil in free or pharmaceutically acceptable salt form. In another embodiment, the NMDA receptor antagonist is memantine in free or pharmaceutically acceptable salt form.

In the seventh aspect of the invention, the combination of a Compound of the Invention and one or more second therapeutic agents as described in Methods I-A, II-A or any of 9.1-9.38, may be administered as a Pharmaceutical Composition or a depot Composition as hereinbefore described. Similarly, the combination of a Compound of the Invention and one or more second therapeutic agents as described in Methods $I_p$-A, II-A or any of 9.1-9.38, may be administered as a Pharmaceutical Composition or a depot Composition as hereinbefore described. The combination compositions can include mixtures of the combined drugs, as well as two or more separate compositions of the drugs, which individual compositions can be, for example, co-administered together to a patient.

In a particular embodiment, Methods I-A, II-A, $I_p$-A, II-A or any of 9.1-9.38 comprises administering to a patient in need thereof, a Compound of the Invention in combination with an atypical antipsychotic agent, e.g., a compound selected from clozapine, aripiprazole, olanzapine, quetiapine, risperidone, ziprasidone, or paliperidone, in free or pharmaceutically acceptable salt form, for example wherein the dosage of the atypical antipsychotic agent is reduced and/or side effects are reduced.

In another embodiment, Methods I-A, II-A, Methods I$_p$-A, II-A or any of 9.1-9.38 comprises administering to a patient in need thereof, a Compound of the Invention in combination with an anti-depressant, e.g., amitriptyline, amoxapine, bupropion, citalopram, clomipramine, desipramine, doxepin, duloxetine, escitalopram, fluoxetine, fluvoxamine, imipramine, isocarboxazid, maprotiline, mirtazapine, nefazodone, nortriptyline, paroxetine, phenelazine sulfate, protriptyline, sertraline, tranylcypromine, trazodone, trimipramine, or venlafaxine, in free or pharmaceutically acceptable salt form. Alternatively, the anti-depressant may be used as an adjunct medication in addition to the compounds of the Invention.

In still another embodiment, Methods I-A, II-A, I$_p$-A, II-A or any of 9.1-9.38 comprises administering to a patient in need thereof, a Compound of the Invention in combination with a compound that modulates GABA activity, e.g., a compound selected from doxepin, alprazolam, bromazepam, clobazam, clonazepam, clorazepate, diazepam, flunitrazepam, flurazepam, lorazepam, midazolam, nitrazepam, oxazepam, temazepam, triazolam, indiplon, zopiclone, eszopiclone, zaleplon, Zolpidem, gabaxadol, vigabatrin, tiagabine, EVT 201 (Evotec Pharmaceuticals), estazolam or any combinations thereof, in free or pharmaceutically acceptable salt form.

In another particular embodiment, Methods I-A, II-A, I$_p$-A, II-A or any of 9.1-9.38 comprises administering to a patient in need thereof, a Compound of the Invention in combination with doxepin in free or pharmaceutically acceptable salt form. Dosages of doxepin can vary in any range known to a person of ordinary skill in the art. In one example, a 10 mg dose of doxepin may be combined with any dosage of a compound of the Invention.

In another embodiment, Methods I-A, II-A, I$_p$-A, II-A or any of 9.1-9.38 comprises administering to a patient in need thereof, a Compound of the Invention in combination (including as part of a daily dosage regimen) with an atypical stimulant, e.g., a modafinil, adrafinil, or armodafinil. A regimen incorporating a Compound of the Invention with such drugs promotes more regular sleep, and avoids side effects such as psychosis or mania associated with higher levels of such drugs, e.g., in the treatment of bipolar depression, cognition associated with schizophrenia, and excessive sleepiness and fatigue in conditions such as Parkinson's disease and cancer.

In the eighth aspect, the invention provides use of a compound as described in the following formulae:
  11.1 Compound of Formula I or any of formulae 1-1.9, in free or pharmaceutically acceptable salt form;
  11.2 a Pharmaceutical Composition as hereinbefore described;
  11.3 Depot Composition as hereinbefore described; or
  11.4 Osmotic-controlled Release Oral delivery System Composition as hereinbefore described,
(in the manufacture of a medicament) for the treatment or prophylaxis of one or more disorders as disclosed hereinbefore, e.g., in any of Method I, any of 7.1-7.32, Method II, any of 8.1-8.15, Methods I-A, II-A, any of 9.1-9.38, Method I$_P$, Methods I$_P$-A, or any methods described in the sixth or seventh aspect of the invention.

In the ninth aspect, the invention provides a pharmaceutical composition as hereinbefore described, e.g., in the following formulae:
  12.1 a Pharmaceutical Composition as hereinbefore described;
  12.2 Depot Composition as hereinbefore described; or
  12.3 Osmotic-controlled Release Oral delivery System Composition as hereinbefore described,
for use in the treatment or prophylaxis of one or more disorders as disclosed hereinbefore, e.g., in any of Method I, any of 7.1-7.32, Method II, any of 8.1-8.15, Methods I-A, II-A, any of 9.1-9.38, Method I$_P$, Methods I$_P$-A, or any methods described in the sixth or seventh aspect of the invention.

DETAILED DESCRIPTION OF THE INVENTION

If not otherwise specified or clear from context, the following terms as used herein have the following meetings:
  a. "Residual symptoms" as used herein include negative symptoms and general psychopathology symptoms as described in the Positive and Negative Symptom Scale (PANSS) for Schizophrenia described in Kay et al., *Schizophr. Bull.* (1987) 13(2):261-276, the contents of which are incorporated by reference in their entirety. Negative symptoms include: blunted affect, emotional withdrawal, poor rapport, passive/apathetic social withdrawal, difficulty in abstract thinking, lack of spontaneity and flow of conversation and stereotyped thinking. General psychopathology symptoms include: somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance. Residual symptoms may also include depression, cognitive impairment and sleep disorders (e.g., insomnia). Of these residual symptoms, the compounds of the invention are particularly useful for the treatment of passive social withdrawal, stereotyped thinking, somatic concerns, anxiety, tension, active social avoidance and depression. Therefore, the compounds of the present invention are particularly useful in improving social integration and social function in patients suffering from schizophrenia. Treatment of these residual symptoms is also particularly effective in schizophrenic patients also suffering from depression.

Unless otherwise indicated, the Compounds of the Invention, e.g., Compounds of Formula I or any of 1-1.9, or any of formulae 4.1-4.4 may exist in free or salt, e.g., as acid addition salts, form. An acid-addition salt of a compound of the invention which is sufficiently basic, for example, an acid-addition salt with, for example, an inorganic or organic acid, for example hydrochloric, hydrobromic, sulphuric, phosphoric, acid acetic, trifluoroacetic, citric, maleic acid, toluene sulfonic, propionic, succinic, glycolic, stearic, lactic, malic, tartaric, citric, ascorbic, palmoic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic acid, and the like. In addition a salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)-amine. In a particular embodiment, the salt of the Compounds of the Invention is a toluenesulfonic acid addition salt. In another particular embodiment, the salt of the Compounds of the Invention is a fumaric acid addition salt. In a particular embodiment, the salt of the Compounds of the Invention is a phosphoric acid addition salt.

The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention, and are therefore also included.

The Compounds of the Invention may comprise one or more chiral carbon atoms. The compounds thus exist in individual isomeric, e.g., enantiomeric or diastereomeric form or as mixtures of individual forms, e.g., racemic/diastereomeric mixtures. Any isomer may be present in which the asymmetric center is in the (R)-, (S)-, or (R,S)-configuration. The invention is to be understood as embracing both individual optically active isomers as well as mixtures (e.g., racemic/diastereomeric mixtures) thereof. Accordingly, the Compounds of the Invention may be a racemic mixture or it may be predominantly, e.g., in pure, or substantially pure, isomeric form, e.g., greater than 70% enantiomeric/diastereomeric excess ("ee"), preferably greater than 80% ee, more preferably greater than 90% ee, most preferably greater than 95% ee. The purification of said isomers and the separation of said isomeric mixtures may be accomplished by standard techniques known in the art (e.g., column chromatography, preparative TLC, preparative HPLC, simulated moving bed and the like).

Geometric isomers by nature of substituents about a double bond or a ring may be present in cis (Z) or trans (E) form, and both isomeric forms are encompassed within the scope of this invention.

Alternatively and/or additionally, the Compounds of the Invention may be included as a depot formulation, e.g., by dispersing, dissolving or encapsulating the Compounds of the Invention in a polymeric matrix as described in the second and third aspect, such that the Compound is continually released as the polymer degrades over time. The release of the Compounds of the Invention from the polymeric matrix provides for the controlled- and/or delayed- and/or sustained-release of the Compounds, e.g., from the pharmaceutical depot composition, into a subject, for example a warm-blooded animal such as man, to which the pharmaceutical depot is administered. Thus, the pharmaceutical depot delivers the Compounds of the Invention to the subject at concentrations effective for treatment of the particular disease or medical condition over a sustained period of time, e.g., 14-180 days, preferably about 30, about 60 or about 90 days.

Polymers useful for the polymeric matrix in the Composition of the Invention (e.g., Depot composition of the Invention) may include a polyester of a hydroxy-fatty acid and derivatives thereof or other agents such as polylactic acid, polyglycolic acid, polycitric acid, polymalic acid, poly-beta.-hydroxybutyric acid, epsilon.-capro-lactone ring opening polymer, lactic acid-glycolic acid copolymer, 2-hydroxybutyric acid-glycolic acid copolymer, polylactic acid-polyethylene glycol copolymer or polyglycolic acid-polyethylene glycol copolymer), a polymer of an alkyl alpha-cyanoacrylate (for example poly(butyl 2-cyanoacrylate)), a polyalkylene oxalate (for example polytrimethylene oxalate or polytetramethylene oxalate), a polyortho ester, a polycarbonate (for example polyethylene carbonate or polyethylenepropylene carbonate), a polyortho-carbonate, a polyamino acid (for example poly-gamma.-L-alanine, poly-.gamma.-benzyl-L-glutamic acid or poly-y-methyl-L-glutamic acid), a hyaluronic acid ester, and the like, and one or more of these polymers can be used.

If the polymers are copolymers, they may be any of random, block and/or graft copolymers. When the above alpha-hydroxycarboxylic acids, hydroxydicarboxylic acids and hydroxytricarboxylic acids have optical activity in their molecules, any one of D-isomers, L-isomers and/or DL-isomers may be used. Among others, alpha-hydroxycarboxylic acid polymer (preferably lactic acid-glycolic acid polymer), its ester, poly-alpha-cyanoacrylic acid esters, etc. may be used, and lactic acid-glycolic acid copolymer (also referred to as poly(lactide-alpha-glycolide) or poly(lactic-co-glycolic acid), and hereinafter referred to as PLGA) are preferred. Thus, in one aspect the polymer useful for the polymeric matrix is PLGA. As used herein, the term PLGA includes polymers of lactic acid (also referred to as polylactide, poly (lactic acid), or PLA). Most preferably, the polymer is the biodegradable poly(d,l-lactide-co-glycolide) polymer.

In a preferred embodiment, the polymeric matrix of the invention is a biocompatible and biodegradable polymeric material. The term "biocompatible" is defined as a polymeric material that is not toxic, is not carcinogenic, and does not significantly induce inflammation in body tissues. The matrix material should be biodegradable wherein the polymeric material should degrade by bodily processes to products readily disposable by the body and should not accumulate in the body. The products of the biodegradation should also be biocompatible with the body in that the polymeric matrix is biocompatible with the body. Particular useful examples of polymeric matrix materials include poly (glycolic acid), poly-D,L-lactic acid, poly-L-lactic acid, copolymers of the foregoing, poly(aliphatic carboxylic acids), copolyoxalates, polycaprolactone, polydioxonone, poly(ortho carbonates), poly(acetals), poly(lactic acid-caprolactone), polyorthoesters, poly(glycolic acid-caprolactone), polyanhydrides, and natural polymers including albumin, casein, and waxes, such as, glycerol mono- and distearate, and the like. The preferred polymer for use in the practice of this invention is dl-(polylactide-co-glycolide). It is preferred that the molar ratio of lactide to glycolide in such a copolymer be in the range of from about 75:25 to 50:50.

Useful PLGA polymers may have a weight-average molecular weight of from about 5,000 to 500,000 daltons, preferably about 150,000 daltons. Dependent on the rate of degradation to be achieved, different molecular weight of polymers may be used. For a diffusional mechanism of drug release, the polymer should remain intact until all of the drug is released from the polymeric matrix and then degrade. The drug can also be released from the polymeric matrix as the polymeric excipient bioerodes.

The PLGA may be prepared by any conventional method, or may be commercially available. For example, PLGA can be produced by ring-opening polymerization with a suitable catalyst from cyclic lactide, glycolide, etc. (see EP-0058481B2; Effects of polymerization variables on PLGA properties: molecular weight, composition and chain structure).

It is believed that PLGA is biodegradable by means of the degradation of the entire solid polymer composition, due to the break-down of hydrolysable and enzymatically cleavable ester linkages under biological conditions (for example in the presence of water and biological enzymes found in tissues of warm-blooded animals such as humans) to form lactic acid and glycolic acid. Both lactic acid and glycolic acid are water-soluble, non-toxic products of normal metabolism, which may further biodegrade to form carbon dioxide and water. In other words, PLGA is believed to degrade by means of hydrolysis of its ester groups in the presence of water, for example in the body of a warm-blooded animal such as man, to produce lactic acid and glycolic acid and create the acidic microclimate. Lactic and glycolic acid are by-products of various metabolic pathways in the body of a warm-blooded animal such as man under normal physiological conditions and therefore are well tolerated and produce minimal systemic toxicity.

In another embodiment, the polymeric matrix useful for the invention may comprise a star polymer wherein the structure of the polyester is star-shaped. These polyesters have a single polyol residue as a central moiety surrounded by acid residue chains. The polyol moiety may be, e. g., glucose or, e. g., mannitol. These esters are known and described in GB 2,145,422 and in U.S. Pat. No. 5,538,739, the contents of which are incorporated by reference.

The star polymers may be prepared using polyhydroxy compounds, e. g., polyol, e. g., glucose or mannitol as the initiator. The polyol contains at least 3 hydroxy groups and has a molecular weight of up to about 20,000 Daltons, with at least 1, preferably at least 2, e. g., as a mean 3 of the hydroxy groups of the polyol being in the form of ester groups, which contain polylactide or co-polylactide chains. The branched polyesters, e. g., poly (d, 1-lactide-co-glycolide) have a central glucose moiety having rays of linear polylactide chains.

The depot composition of the invention as hereinbefore described may comprise the polymer in the form of microparticles or nanoparticles, or in a liquid form, with the Compounds of the Invention dispersed or encapsulated therein. "Microparticles" is meant solid particles that contain the Compounds of the Invention either in solution or in solid form wherein such compound is dispersed or dissolved within the polymer that serves as the matrix of the particle. By an appropriate selection of polymeric materials, a microparticle formulation can be made in which the resulting microparticles exhibit both diffusional release and biodegradation release properties.

In a particular embodiment, the Compound of the Invention is formulated into microparticles of an appropriate size to allow slow release kinetics after intramuscular injection.

When the polymer is in the form of microparticles, the microparticles may be prepared using any appropriate method, such as by a solvent evaporation or solvent extraction method. For example, in the solvent evaporation method, the Compounds of the Invention and the polymer may be dissolved in a volatile organic solvent (for example a ketone such as acetone, a halogenated hydrocarbon such as chloroform or methylene chloride, a halogenated aromatic hydrocarbon, a cyclic ether such as dioxane, an ester such as ethyl acetate, a nitrile such as acetonitrile, or an alcohol such as ethanol) and dispersed in an aqueous phase containing a suitable emulsion stabilizer (for example polyvinyl alcohol, PVA). The organic solvent is then evaporated to provide microparticles with the Compounds of the Invention encapsulated therein. In the solvent extraction method, the Compounds of the Invention and polymer may be dissolved in a polar solvent (such as acetonitrile, dichloromethane, methanol, ethyl acetate or methyl formate) and then dispersed in an aqueous phase (such as a water/PVA solution). An emulsion is produced to provide microparticles with the Compounds of the Invention encapsulated therein. Spray drying is an alternative manufacturing technique for preparing the microparticles.

Another method for preparing the microparticles of the invention is also described in both U.S. Pat. Nos. 4,389,330 and 4,530,840, the contents of which are incorporated by reference.

The microparticle of the present invention can be prepared by any method capable of producing microparticles in a size range acceptable for use in an injectable composition. One preferred method of preparation is that described in U.S. Pat. No. 4,389,330. In this method the active agent is dissolved or dispersed in an appropriate solvent. To the agent-containing medium is added the polymeric matrix material in an amount relative to the active ingredient that provides a product having the desired loading of active agent. Optionally, all of the ingredients of the microparticle product can be blended in the solvent medium together.

Solvents for the Compounds of the Invention and the polymeric matrix material that can be employed in the practice of the present invention include organic solvents, such as acetone; halogenated hydrocarbons, such as chloroform, methylene chloride, and the like; aromatic hydrocarbon compounds; halogenated aromatic hydrocarbon compounds; cyclic ethers; alcohols, such as, benzyl alcohol; ethyl acetate; and the like. In one embodiment, the solvent for use in the practice of the present invention may be a mixture of benzyl alcohol and ethyl acetate. Further information for the preparation of microparticles useful for the invention can be found in U.S. Patent Publication Number 2008/0069885, the contents of which are incorporated herein by reference in their entirety.

The amount of the Compounds of the Invention incorporated in the microparticles usually ranges from about 1 wt % to about 90 wt. %, preferably 30 to 50 wt. %, more preferably 35 to 40 wt. %. By weight % is meant parts of the Compounds of the Invention per total weight of microparticle.

The pharmaceutical depot may comprise a pharmaceutically-acceptable diluent or carrier, such as a water miscible diluent or carrier.

Details of Osmotic-controlled Release Oral delivery System composition may be found in EP 1 539 115 (U.S. Pub. No. 2009/0202631) and WO 2000/35419, the contents of each of which are incorporated by reference in their entirety.

A "therapeutically effective amount" is any amount of the Compounds of the invention (for example as contained in the pharmaceutical depot) which, when administered to a subject suffering from a disease or disorder, is effective to cause a reduction, remission, or regression of the disease or disorder over the period of time as intended for the treatment.

Dosages employed in practicing the present invention will of course vary depending, e.g. on the particular disease or condition to be treated, the particular Compounds of the Invention used, the mode of administration, and the therapy desired.

Compounds of the Invention may be administered by any satisfactory route, including orally, parenterally (intravenously, intramuscular or subcutaneous) or transdermally, but are preferably administered orally. In certain embodiments, the Compounds of the Invention, e.g., in depot formulation, is preferably administered parenterally, e.g., by injection.

In general, satisfactory results for Method I or any of formulae 7.1-7.32 or Method $I_P$ or use of the Compounds of the Invention as hereinbefore described, e.g. for the treatment of a combination of diseases such as a combination of at least depression, psychosis, e.g., (1) psychosis, e.g., schizophrenia, in a patient suffering from depression; (2) depression in a patient suffering from psychosis, e.g., schizophrenia; (3) mood disorders associated with psychosis, e.g., schizophrenia, or Parkinson's disease; and (4) sleep disorders associated with psychosis, e.g., schizophrenia, or Parkinson's disease, as set forth above are indicated to be obtained on oral administration at dosages of the order from about 1 mg to 100 mg once daily, preferably about 2.5 mg-50 mg, e.g., 2.5 mg, 5 mg, 10 mg, 20 mg, 30 mg, 40 mg or 50 mg, once daily, preferably via oral administration.

Satisfactory results for Method II or any of 8.1-8.15, Method II or use of the Compounds of the Invention as hereinbefore described, e.g. for the treatment of sleep disorder alone or agitation, aggressive behaviors, post-traumatic stress disorder or impulse control disorder alone, e.g., intermittent explosive disorder alone are indicated to be obtained on oral administration at dosages of the order from about 1 mg-10 mg once daily, e.g., about 2.5 mg-5 mg, e.g., 2.5 mg, 3 mg, 4 mg, 5 mg or 10 mg, of a Compound of the Invention, in free or pharmaceutically acceptable salt form, once daily, preferably via oral administration.

Satisfactory results for Method I-A or any of 9.1-9.38 or Method $I_P$-A are indicated to be obtained at less than 100 mg, preferably less than 50 mg, e.g., less than 40 mg, less than 30 mg, less than 20 mg, less than 10 mg, less than 5 mg, less than 2.5 mg, once daily. Satisfactory results for Method II-A or any of 9.1-9.38 are indicated to be obtained at less than 10 mg, e.g., less than 5 mg or, preferably less than 2.5 mg.

For treatment of the disorders disclosed herein wherein the depot composition is used to achieve longer duration of action, the dosages will be higher relative to the shorter action composition, e.g., higher than 1-100 mg, e.g., 25 mg, 50 mg, 100 mg, 500 mg, 1,000 mg, or greater than 1000 mg. In a particular embodiment, the dosage regimen for depot composition includes an initial oral immediate dose along with depot release so as to provide a steady-state blood level of the drug. Duration of action of the Compounds of the Invention may be controlled by manipulation of the polymer composition, i.e., the polymer:drug ratio and microparticle size. Wherein the composition of the invention is a depot composition, administration by injection is preferred.

The pharmaceutically acceptable salts of the Compounds of the Invention can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in PCT/US08/03340 and/or U.S. Provisional Appl. No. 61/036,069.

Pharmaceutical compositions comprising Compounds of the Invention may be prepared using conventional diluents or excipients (an example include, but is not limited to sesame oil) and techniques known in the galenic art. Thus oral dosage forms may include tablets, capsules, solutions, suspensions and the like.

All references herein to dosage, dosage rate or therapeutically effect amount of a Compound or Composition of the Invention refers to the equivalent free-base or pharmaceutically acceptable salt form moiety in the dosage.

The in-vitro metabolism of the Compound of the Formula Q and its metabolites is studied using subcellular fractions and isolated hepatocytes. The results indicate that the Compound of Formula Q is N-demethylated to the Compound of Formula R via the P450 cytochrome oxidase isoform 3A4 (CYP 3A4), and that both the Compound of Formula Q and the Compound of Formula R undergo ketone reduction via the enzyme ketone reductase, to form the Compounds of Formula S and T, respectively. These two reductions are both catalyzed in the reverse direction (oxidation) by CYP 3A4. These results are summarized in the scheme below:

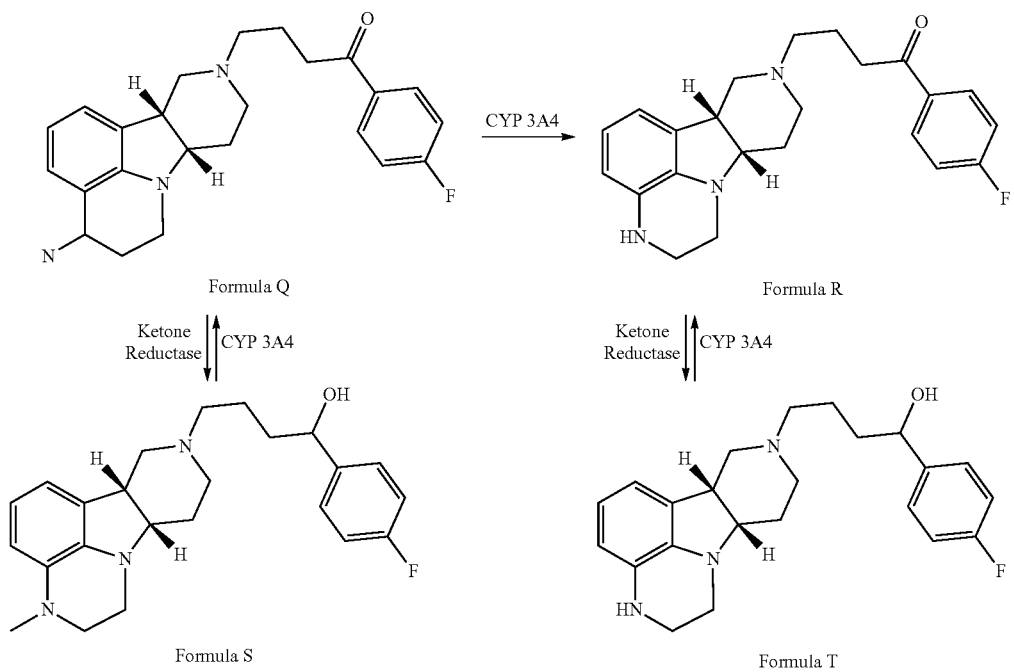

In addition, the in-vivo metabolism of the Compound of Formula Q is studied after oral administration to rats, dogs and humans. Plasma levels after administration are determined in all three species for the Compounds of Formula Q through T. The results of the studies indicate that metabolism of the Compound of Formula Q is rapid, and that the N-demethyl compounds are highly polar and excreted rapidly. Results of human plasma studies on day 8 after 7 day dosing (120 mg, 4 doses/day) with the Compound of Formula Q are shown below:

| Analyte | Tmax (hrs) | Cmax (ng/mL) | AUC (hrs * ng/mL) |
|---|---|---|---|
| Compound Q | 2.5 | 78 | 347 |
| Compound S | 3.5 | 79 | 906 |
| Compound R | 2.5 | 37 | 170 |
| Compound T | 6.0 | 38 | 517 |

Methods of Making the Compounds of the Invention:

The intermediates of the Compounds of the Invention may be prepared as described in in WO PCT/US08/03340 (WO 2008/112280); U.S. application Ser. No. 10/786,935; U.S. Pat. Nos. 6,548,493; 7,238,690; 6,552,017; 6,713,471; 7,183,282; U.S. RE39680, and U.S. RE39679, the contents of which are incorporated by reference in their entirety. Salts of the Compounds of the Invention may also be prepared as similarly described in U.S. Pat. Nos. 6,548,493; 7,238,690; 6,552,017; 6,713,471; 7,183,282; U.S. RE39680; U.S. RE39679; and WO 2009/114181, the contents of each of which are incorporated by reference in their entirety.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

The Compounds of Formula I can be prepared by standard methods known to those skilled in the art. U.S. Pat. No. 8,309,722, which is incorporated by reference in its entirety, discloses the synthesis of the Compound of Formula Q, and all of the intermediates therefor:

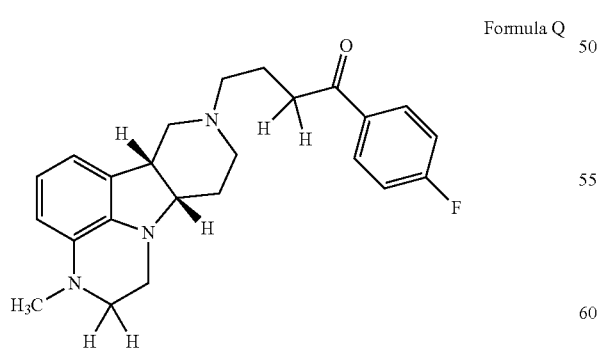

Formula Q

The Compounds of the Invention are synthesized in similar manner to the methods disclosed for the synthesis of the Compound of Formula Q. Examples of these syntheses follow.

For example, Compound B may be prepared from Compound A (disclosed in the U.S. Pat. No. 8,309,722) by reacting with d3-iodomethane in the presence of a base, such as potassium carbonate, in a suitable solvent, such as acetone. Following the procedures of U.S. Pat. No. 8,309,722, Compound B can then be converted to a Compound of Formula I, wherein $R^1$ is CD3. The reaction may be summarized in the reaction scheme below:

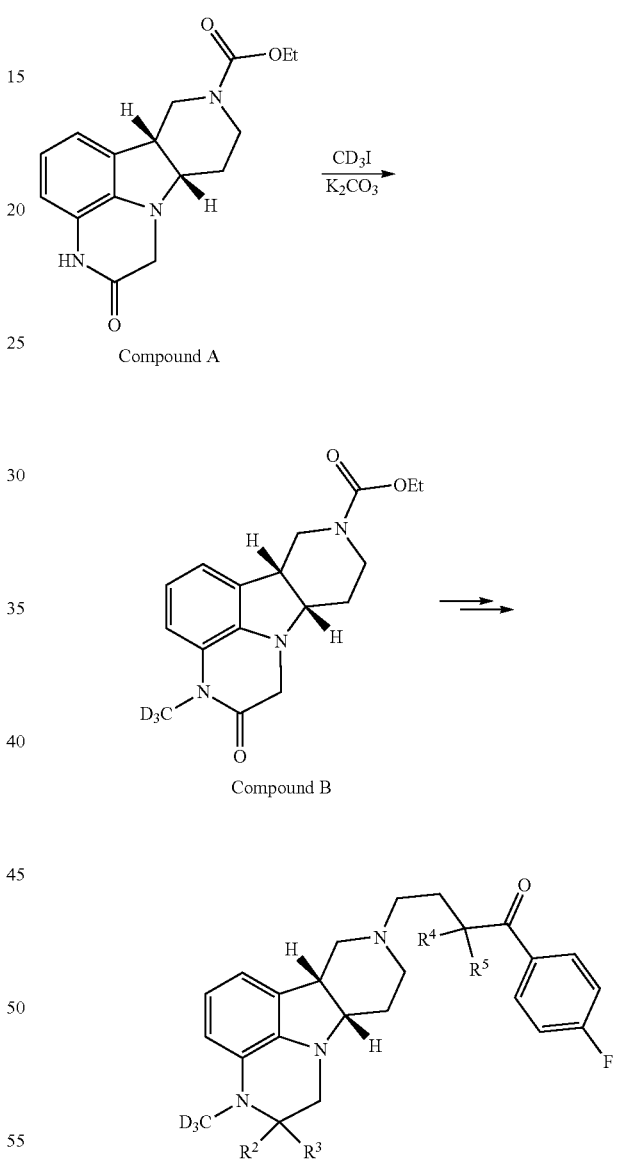

For example, Compound D may be prepared from a Compound of Formula C (disclosed in the U.S. Pat. No. 8,309,722, and herein) by reacting with d3-borane THF complex, in a suitable solvent, such as tetrahydrofuran. Following the procedures of U.S. Pat. No. 8,309,722, Compound D can then be converted a Compound of Formula I, wherein $R^2$ and $R^3$ are D. The reaction may be summarized in the reaction scheme below:

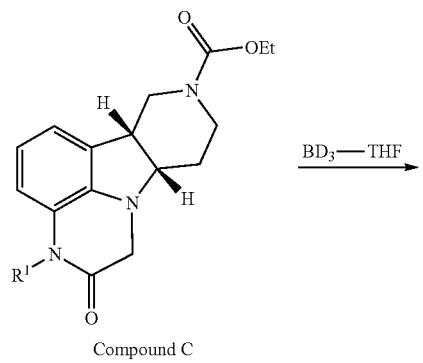

Compound C

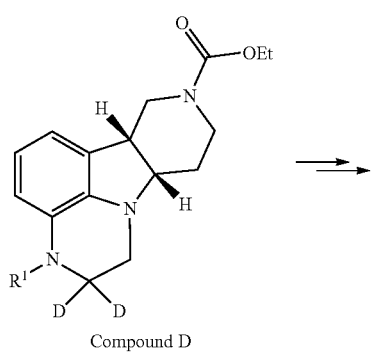

Compound D

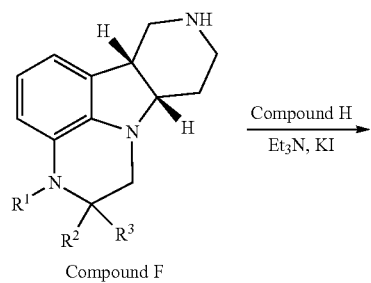

Compound F

For example, a Compound of Formula I, wherein $R^4$ and $R^5$ are D, may be prepared from a Compound of Formula F (disclosed in the U.S. Pat. No. 8,309,722, and herein) by reacting with Compound H, as defined hereinafter, in the presence of potassium iodide and a base, such as potassium carbonate and triethylamine, in a suitable solvent, such as 3-pentanone. Following the procedures of U.S. Pat. No. 8,309,722, the product can be isolated and purified. The reaction may be summarized in the reaction scheme below:

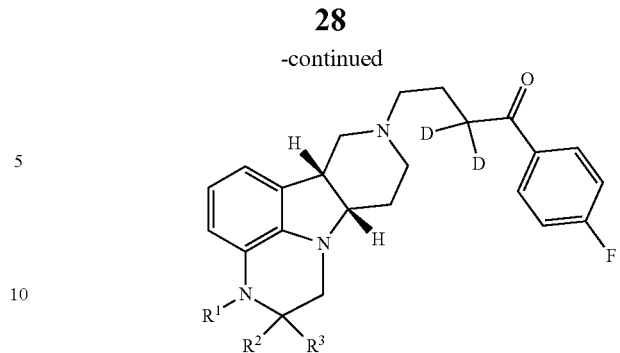

A Compound of Formula H can be prepared essentially according to the procedure of J. R. Cabrero-Antonino (*Chemistry: A European Journal*, Vol 18, No. 35, p.11107-11114, 27 Aug. 2012). Iron (III) chloride and silver bisaminotriflate in dioxane are stirred at room temperature for 30 minutes, and then 1-(4-chlorobut-1-yn-1-yl)-4-fluorobenzene and deuterium oxide are added. The mixture is heated at 80° C. for 18 hours to give Compound H. The reaction may be summarized in the reaction scheme below:

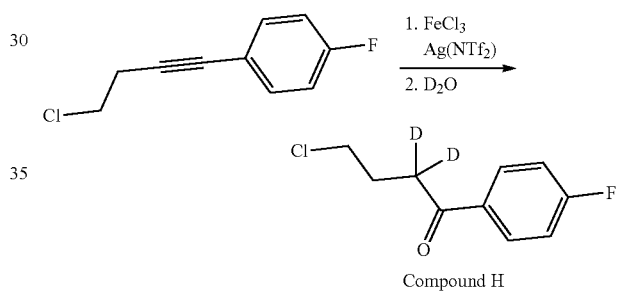

Compound H

A Compound of Formula II, wherein $R^4$ and $R^5$ are H, and $R^6$ to $R^9$ are D, may be prepared from a Compound of Formula F (disclosed in the U.S. Pat. No. 8,309,722, and herein) by reacting with Compound J, as defined hereinafter, in the presence of potassium iodide and a base, such as potassium carbonate and triethylamine, in a suitable solvent, such as 3-pentanone. Following the procedures of U.S. Pat. No. 8,309,722, the product can be isolated and purified. The reaction may be summarized in the reaction scheme below:

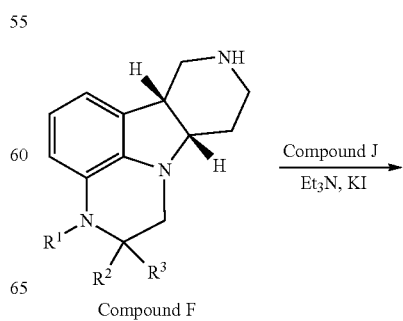

Compound F

-continued

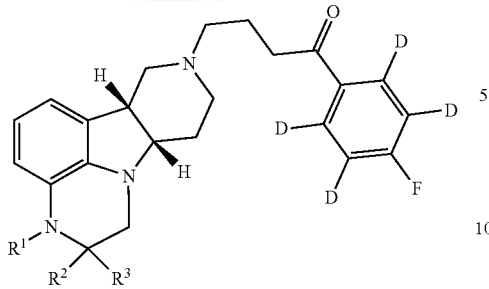

A Compound of Formula J can be prepared by reacting ds-fluorobenzene with 4-chlorobutanoyl chloride in the presence of aluminum (III) chloride in a suitable solvent, such as carbon tetrachloride. The reaction may be summarized in the reaction scheme below:

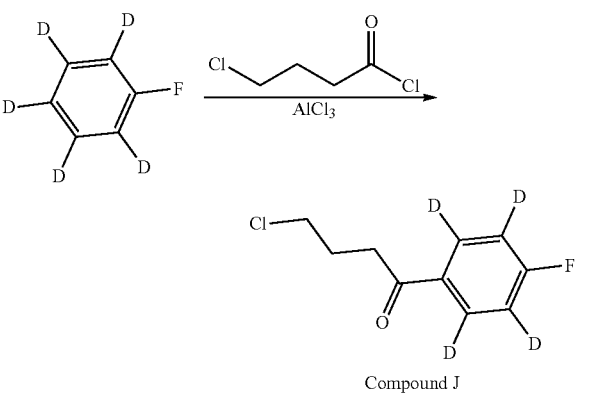

Compound J

The invention claimed is:

1. A method for the treatment of a central nervous system disorder selected from anxiety, depression, psychosis, schizophrenia, post-traumatic stress disorder, impulse control disorders and intermittent explosive disorder, comprising administering to a patient in need thereof a therapeutically effective amount of compound of formula I:

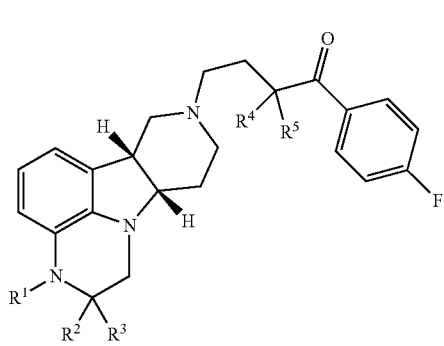

Formula I wherein:

$R^1$ is $CH_3$;

$R^2$ and $R^3$ are each independently H or D;

$R^4$ and $R^5$ are each H;

provided that $R^2$ and $R^3$ are not both H, and wherein D is deuterium;

in free or salt form.

2. The method according to claim 1, wherein $R^2$ and $R^3$ are both D.

3. The method according to claim 1, wherein $R^2$ is D and $R^3$ is H.

4. The method according to claim 1, wherein said compound is in salt form.

5. The method according to claim 4, wherein the salt is a toluenesulfonic acid addition salt.

6. The method according to claim 1, wherein the method comprises administering the compound of Formula I as a pharmaceutical composition comprising the compound in free or pharmaceutically acceptable salt form, in combination or association with a pharmaceutically acceptable diluent or carrier.

7. The method according to claim 1, wherein said disorder is selected from a group consisting of anxiety, depression, psychosis, and schizophrenia.

8. The method according to claim 7, wherein said disorder is schizophrenia.

9. The method according to claim 7, wherein said disorder is anxiety.

10. The method according to claim 8, wherein the patient is suffering from residual symptoms of schizophrenia.

11. The method according to claim 10, wherein said residual phase symptoms are selected from negative symptoms such as blunted affect, emotional withdrawal, poor rapport, passive or apathetic social withdrawal, difficulty in abstract thinking, lack of spontaneity and flow of conversation and stereotyped thinking; general psychopathology symptoms such as somatic concern, anxiety, guilt feelings, tension, mannerisms and posturing, depression, motor retardation, uncooperativeness, unusual thought content, disorientation, poor attention, lack of judgment and insight, disturbance of volition, poor impulse control, preoccupation and active social avoidance; cognitive impairment and sleep disorders.

12. The method according to claim 1, wherein said disorder is depression.

13. The method according to claim 12, wherein said depression is bipolar disorder.

* * * * *